United States Patent [19]

Anderson et al.

[11] Patent Number: 5,098,466
[45] Date of Patent: Mar. 24, 1992

[54] COMPOUNDS

[75] Inventors: Richard J. Anderson, Palo Alto; Michael M. Leippe, Boulder Creek; Joe T. Bamberg, Palo Alto, all of Calif.

[73] Assignee: Sandoz Ltd., Basel, Switzerland

[21] Appl. No.: 570,573

[22] Filed: Aug. 21, 1990

Related U.S. Application Data

[63] Continuation-in-part of Ser. No. 307,661, Feb. 6, 1989, abandoned, which is a continuation-in-part of Ser. No. 74,197, Jul. 16, 1987, abandoned, which is a continuation-in-part of Ser. No. 9,963, Feb. 2, 1987, abandoned, which is a continuation-in-part of Ser. No. 894,990, Aug. 8, 1986, abandoned, which is a continuation-in-part of Ser. No. 767,465, Aug. 20, 1985, abandoned.

[51] Int. Cl.$^5$ ............... C07D 213/55; A01N 43/40
[52] U.S. Cl. .................. 71/94; 71/90; 71/92; 71/95; 71/88; 546/322; 546/316; 546/315; 546/194; 546/263; 546/277; 546/280; 546/281; 548/214; 548/201; 548/127; 548/343; 544/335; 544/406; 544/131; 544/54; 549/71; 549/484
[58] Field of Search ................ 546/322, 315, 316, 22; 71/94

[56] References Cited

U.S. PATENT DOCUMENTS 4,493,930  1/1985  Klayman et al. .................. 544/360

FOREIGN PATENT DOCUMENTS 0034010  8/1981  European Pat. Off. .

OTHER PUBLICATIONS

Runti et al., Farmaw Ed. Sci., pp. 260–268, Apr. 1987.
French et al., J. Med. Chem. 1974, vol. 17, No. 2, pp. 172–181.

*Primary Examiner*—Jane T. Fan
*Attorney, Agent, or Firm*—Allen E. Norris

[57] ABSTRACT

Substituted semicarbazones, thiosemicarbazones and isothiosemicarbazones and salts thereof, intermediates therefor, synthesis thereof, and the use of said compounds for the control of weeds.

35 Claims, No Drawings

COMPOUNDS

This is a continuation-in-part of Ser. No. 07/307,661, filed Feb. 6, 1989, now abandoned, which is a continuation-in-part of Ser. No. 07/074,197, filed July 16, 1987, now abandoned, which is a continuation-in-part of Ser. No. 07/009,963, filed Feb. 2, 1987, now abandoned, which is a continuation-in-part of Ser. No. 06/894,990, filed Aug. 8, 1986, now abandoned, which is a continuation-in-part of Ser. No. 06/767,465, filed Aug. 20, 1985, now abandoned the entire enclosures of which are incorporated herein by reference.

This invention relates to novel substituted semicarbazones, thiosemicarbazones and isothiosemicarbazones and salts thereof, intermediates therefor, synthesis thereof, and the use of said compounds for the control of weeds.

More particularly, the compounds of the present invention are represented by the following formula (A):

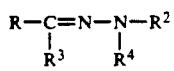

(A)

wherein,
R is the group

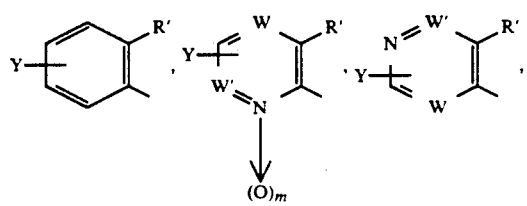

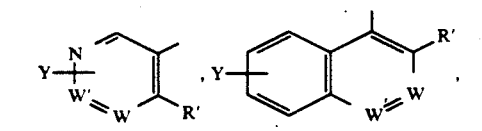

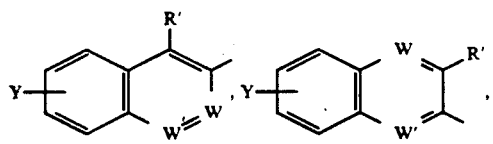

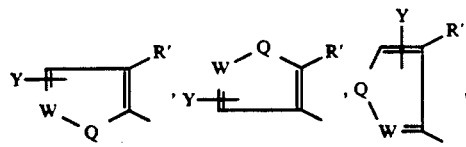

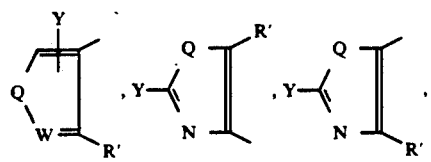

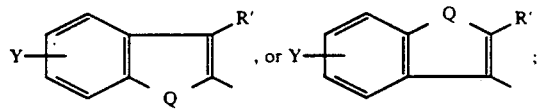

R' is the group

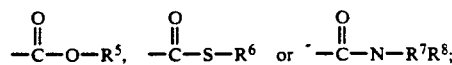

$R^2$ is the group

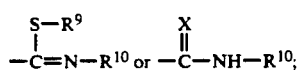

each of $R^3$ and $R^4$ is independently hydrogen or lower alkyl;

$R^5$ is hydrogen, lower alkyl, lower haloalkyl, lower alkoxyalkyl, unsubstituted or substituted phenyl, alkali or alkali earth metal cation, ammonium cation, substituted ammonium cation, phosphonium cation, trialkylsulfonium cation, trialkylsulfoxonium cation or the group

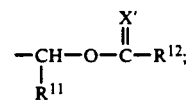

each of $R^6$ and $R^9$ is lower alkyl, lower alkenyl, phenyl or benzyl;

each of $R^7$ and $R^8$ is independently hydrogen or lower alkyl; or $R^7$ and $R^8$ are taken together to form a lower alkylene bridge of three to six carbon atoms, optionally including one of O, S or NH in the ring;

$R^{10}$ is the group

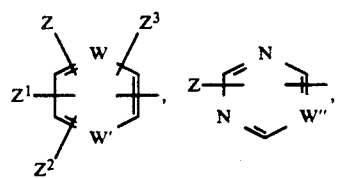

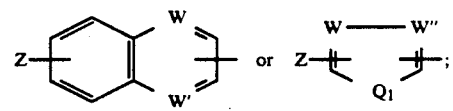

each of $R^{11}$ and $R^{12}$ is independently hydrogen or lower alkyl or lower alkoxyalkyl;

m is zero or one;

Q is oxygen, sulfur or N-$R^{13}$;

$R^{13}$ is hydrogen or lower alkyl;

each of W, W' and W''' is nitrogen or CH;

each of X and X' is independently oxygen or sulfur; and each of Y, Z, $Z^1$, $Z^2$ and $Z^3$ is independently hydrogen, lower alkyl, lower haloalkyl, lower alkoxy, lower haloalkoxy, lower alkenyloxy, lower haloalkenyloxy, lower alkynyloxy, lower alkylthio, phenyl, phenoxy, hydroxy, halogen, nitro, cyano, amino, lower alkylamino or dialkylamino;

with the proviso that when R is phenyl, then $R^3$ cannot be hydrogen.

In the description and claims hereinafter, each of m, Q, $R$-$R^{13}$, W-W''', X, X', Y, and Z-$Z^3$ is as defined above, unless otherwise noted.

The compounds of the present invention of formula (A) where

may be synthesized as outlined below:

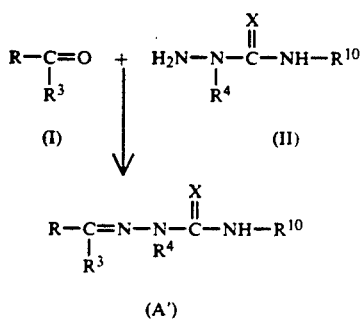

In the above synthesis, the carbonyl compound (I) and the semicarbazide or thiosemicarbazide (II) are reacted together at room temperature in the presence of an alcohol solvent such as methanol or ethanol and with or without an acid catalyst to give the semicarbazones (A').

Some of the semicarbazides and thiosemicarbazides of formula (II) are known compounds, such as those where $R^{10}$ is optionally substituted phenyl. Others of formula (II), such as where $R^{10}$ is optionally substituted pyridyl, are new compounds. Generally, the semicarbazides and thiosemicarbazides can be synthesized by the reaction of hydrazine hydrate with either:

a) an isocyanate or isothiocyanate of formula (IV) in an organic solvent at a temperature below room temperature, or b) a carbamate or thiocarbamate of formula (V) (where $R^{20}$ is lower alkyl or phenyl) in an organic solvent and at reflux temperature, or c) a urea of formula (VI) in an organic solvent and at reflux temperature.

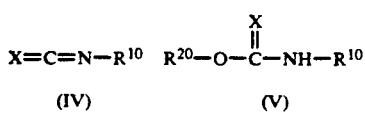

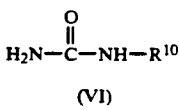

The following terms, wherever used in the description herein and in the appended claims, have the meaning defined below, unless otherwise specified hereinafter.

The term "lower alkyl" refers to an alkyl group, straight or branched, having a chain length of one to eight carbon atoms.

The term "lower alkoxy" refers to an alkoxy group, straight or branched, having a chain length of one to eight carbon atoms.

The term "lower haloalkyl" refers to a lower alkyl group substituted with one to six halogen atoms.

The term "lower haloalkoxy" refers to a lower alkoxy group substituted with one to six halogen atoms.

The term "lower alkylthio" refers to a lower alkylthio group, straight or branched, having a chain length of one to eight carbon atoms.

The term "lower alkoxyalkyl" refers to a lower alkyl group substituted with a lower alkoxy group, the total number of carbon atoms being two to ten.

The term "lower alkylamino" refers to a lower alkyl group substituted with an amino group.

The term "lower alkenyl" refers to an alkenyl group straight or branched, having one or two ethylenic bonds and having a chain length of two to eight carbon atoms.

The term "substituted phenyl" refers to a phenyl ring substituted at one to three of the ring carbon atoms with a group selected from lower alkyl, lower haloalkyl, lower alkoxy, lower haloalkoxy or halogen.

The term "substituted ammonium cation" refers to an ammonium cation substituted by a $C_{1-20}$alkyl, di-$C_{1-20}$alkyl, tri-$C_{1-20}$alkyl, tetra-$C_{1-20}$alkyl, hydroxy-$C_{1-5}$alkyl, di(hydroxy-$C_{1-5}$alkyl), tri(hydroxy-$C_{1-5}$alkyl), $C_{1-5}$alkoxy-$C_{1-5}$alkyl, hydroxy-$C_{1-5}$alkoxy-$C_{1-5}$alkyl or $C_{1-5}$alkoxycarbonyl-$C_{1-5}$alkyl group.

Compounds of the present invention wherein $R_4$ represents hydrogen have the potential to exist in one of three tautomeric forms, i.e.

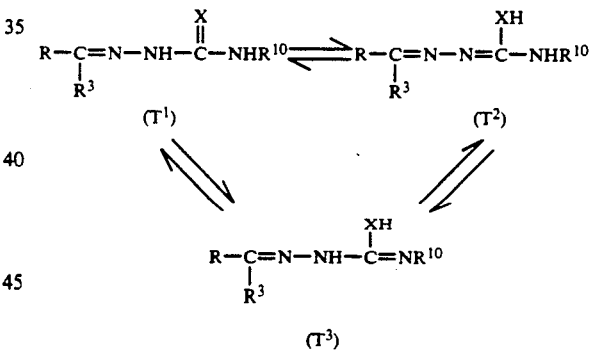

When $R^4$ represents lower alkyl only $T^1$ and $T^3$ form may exist. Although the tendency toward one or other tautomeric form will depend on substitution pattern and the like, form $T^1$ is thought to predominate. When preparing compound of formula A wherein $R^5$ is a salt or an ester these may be obtained as di-salts or di-esters in $T^2$ or $T^3$ form. When $R^2$ represents

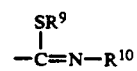

and $R^4$ is hydrogen the compounds may exist in $T^2$ or $T^3$ form (XH being replaced by $SR^9$). The compounds of formula A may further exist in either the syn or the anti-form, although the anti-form usually predominates. The present invention is intended to cover tautomeric/isomeric forms and mixtures thereof.

The novel compounds of formula (A) are useful for the control of weeds, using pre- and/or post-emergent treatments. They are also useful as plant growth regulators. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one hundredth to 10 pounds per acre especially five hundredths to ten pounds e.g. one-tenth or less to ten pounds per acre. The application of a compound of the present invention to the "locus" of the weed includes application to the seeds, the plant (weed) or parts of the plant, or the soil.

When employed as plant growth regulators the compounds exhibit effects such as vegetative growth reduction, seed head suppression and fruit structure modification at rates of less than 0.05 lbs/acre to as low as 0.0001 lbs/acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

While some of the compounds of the present invention have significant activity on grass weeds, the compounds, in general, demonstrate a higher level of herbicidal activity on broadleaf plants when applied post-emergence. Broadleaf plant (weed) species on which the compounds of the present invention show effective herbicidal activity include, but are not limited to, mustard, pigweed, velvetleaf, jimsonweed, cocklebur, sicklepod, annual morning glory, lambsquarter, teaweed and smartweed.

The compounds of the present invention, when applied pre-emergence, demonstrate high levels of herbicidal activity on both broadleaf and grass weeds.

The compounds of formula A in which R is an optionally substituted isothiazole or optionally substituted pyridine are suitable for the selective control of weeds in certain crop plants. These compounds are particularly suitable for use in a corn locus.

Compounds of this invention may be advantageously combined with other herbicides for broadspectrum weed control. Examples of herbicides which can be combined with a compound of the present invention include those selected from the carbamates, thiocarbamates, chloroacetamides, triazines, dinitroanilines, benzoic acids, glycerol ethers, pyridazinones, uracils and ureas, picolinic acids, phenoxys, amides, nitriles, diphenyl ethers, imidazolinones, sulfonylureas, cyclohexanediones, aryloxyphenoxys, bipyridilium, isoxazolones and others for controlling a broad spectrum of weeds.

The following examples are provided to illustrate the practice of the present invention. Temperature is given in degrees Centigrade. "RT" means room temperature. Parts and percentages are by weight. The symbols *, # and + when used in connection with melting points mean "gas", "softens" and "decomposes", respectively.

FINAL PRODUCTS

EXAMPLE 1

To a solution of 2-acetylnicotinic acid (0.40 g, 2.4 mmol) in 7 ml of methanol is added a solution of 4-phenylsemicarbazide (0.37 g, 2.4 mmol) in 5 ml of methanol. The mixture is stirred at RT overnight, after which the solid precipitate is collected by filtration, washed with ethanol and dried to give 2-acetyl-nicotinic acid 4-phenylsemicarbazone, m.p. 174° (dec.) (compound 1, Table A).

EXAMPLE 2

2-Acetylbenzoic acid (0.50 g, 3.0 mmol) and 2-methyl-4-(3-trifluoromethyl)phenylsemicarbazide (0.67 g, 3.0 mmol) are dissolved together in 15 ml of ethanol. After 3 hours at RT, 50 mg of pyridyl tosylate is added. After 2 more hours, the precipitated solid is collected by filtration and dried to give 2-acetylbenzoic acid 2-methyl-4-(3-trifluoromethylphenyl)-semicarbazone, m.p. 172° (gas) (compound 2, Table A).

EXAMPLE 3

Following the procedure of either Example 1 or Example 2, each of the semicarbazone or thiosemicarbazone compounds 3-47, 155-161, 217, 218 and 240-243 under Table A, 48-52, 203-205 and 210 under Table B, 63-79 under Table C, 87-100 under Table D, and 105-144, 174-189, 213-216 and 221-237 under Table E is prepared from the corresponding semicarbazide or thiosemicarbazide and acetyl compound.

EXAMPLE 4 a) To a solution of 2-acetylnicotinic acid 4-phenylsemicarbazone (0.32 g) in 5 ml of methanol is added 1 equivalent of sodium methoxide. The mixture is stirred at RT for 5 min., after which the solvent is removed by roto-evaporation to give the sodium salt of 2-acetyl-nicotinic acid 4-phenyl-semicarbazone, m.p. 203° (dec.) (of compound 1 the sodium salt).

By employing 2 equivalents of sodium methoxide the di-Na+ of compound #4 may be obtained m.p. 220° (softens), 230°-235° (gas).

b) Analogously to a) using 2-acetylnicotinic acid 4-(3-fluorophenyl)semicarbazone (compound 4) or 2-acetylnicotinic acid 4-(3,5-difluorophenyl)semicarbazone (compound 31) in methanol and 1 equivalent of potassium methoxide the potassium salt of compound 4 m.p. >280° and of compound 31 m.p. >300° are obtained.

Following the above procedures, each of the acids under Tables A, B, C, D, E and F is treated with 1 equivalent of sodium methoxide to give the corresponding sodium salt.

EXAMPLE 5

To 2-acetylnicotinic acid 4-phenylsemicarbazone (0.32 g) in 5 ml of methanol is added 1 equivalent of an aqueous solution of ammonium hydroxide. The mixture is stirred at RT for 5 min., after which the solvent is removed by rotoevaporation to give the ammonium salt of 2-acetylnicotinic acid 4-phenylsemicarbazone, m.p. 146°-150° (softens) and 198°-200° (gas) (of compound 1 the ammonium salt). The following compounds may be prepared analogously.

Of compound 50, the ammonium salt m.p. 190° (softens), 208°-215° (gas)

Of compound 52, the ammonium salt m.p. 145° (softens), 167°-170° (gas)

Of compound 141, the ammonium salt m.p. 200°-208° (softens), 230° (gas).

Following the above procedures, each of the acids under Tables A, B, C, D, E and F is treated with 1 equivalent of aqueous ammonium hydroxide to give the corresponding ammonium salt.

EXAMPLE 6

Following the procedures of Example 5, using isopropylamine, 2-hydroxyethylamine, di-2-hydroxyethylamine, tri-2-hydroxyethylamine, diisopropylamine, 2-(2-hydroxyethoxy)ethylamine, dimethylamine, octylamine, tetradecylamine, piperidine, methylglycine or aminopropylmorpholine, the following salts are obtained:

Of compound 1, the isopropylammonium salt, m.p. 94° (softens), 120° (gas)

Of compound 3, the isopropylammonium salt, m.p. 148°-150°

Of compound 4, the isopropylammonium salt, m.p. 111°-118°

Of compound 31, the isopropylammonium salt, m.p. 111°-113°

Of compound 104, the isopropylammonium salt, m.p. 300°

Of compound 141, the isopropylammonium salt, m.p. 113°-122°

Of compound 153, the isopropylammonium salt, m.p. 98°-110°

Of compound 154, the isopropylammonium salt, m.p. 151° (gas)

Of compound 195, the isopropylammonium salt, m.p. 61°-63°

Of compound 196, the isopropylammonium salt, m.p. 70°-73°

Of compound 197, the isopropylammonium salt, m.p. 57°-60°

Of compound 198, the isopropylammonium salt, m.p. 66°-68°

Of compound 204, the isopropylammonium salt, m.p. 265°-269° (dec)

Of compound 1, the 2-hydroxyethylammonium salt, m.p. 131° (gas)

Of compound 3, the 2-hydroxyethylammonium salt, m.p. 159°-164° (dec)

Of compound 4, the 2-hydroxyethylammonium salt, m.p. 164°-166°

Of compound 22, the 2-hydroxyethylammonium salt, m.p. 118° (gas)

Of compound 30, the 2-hydroxyethylammonium salt, m.p. 158° (softens), 201°-104°

Of compound 31, the 2-hydroxyethylammonium salt m.p. 190°-193°

Of compound 141, the 2 hydroxyethylammonium salt, m.p. 78°-86°

Of compound 184, the 2-hydroxyethylammonium salt, m.p. 165° (gas)

Of compound 185, the 2-hydroxyethylammonium salt, m.p. 75° (softens), 95°

Of compound 186, the 2-hydroxyethylammonium salt, m.p. 82°-84°

Of compound 3, the di-2-hydroxyethylammonium salt, m.p. 134°-185°

Of compound 4, the di-2-hydroxyethylammonium salt, m.p. 184°-186°

Of compound 30, the di-2-hydroxyethylammonium salt, m.p. 127° (gas)

Of compound 31, the di-2-hydroxyethylammonium salt, m.p. 172°-175° (gas)

Of compound 141, the di-2-hydroxyethylammonium salt, m.p. 174°

Of compound 142, the di-2-hydroxyethylammonium salt, m.p. 168°

Of compound 153, the di-2-hydroxyethylammonium salt, m.p. 108° (softens), 112° (dec)

Of compound 179, the di-2-hydroxyethylammonium salt, m.p. 162°-168°

Of compound 184, the di-2-hydroxyethylammonium salt, m.p. 168° (gas)

Of compound 185, the di-2-hydroxyethylammonium salt, m.p. 148°-151°

Of compound 186, the di-2-hydroxyethylammonium salt, m.p. 168°-170°

Of compound 188, the di-2-hydroxyethylammonium salt, m.p. 48°-70° (sinters), 157°-161°

Of compound 195, the di-2-hydroxyethylammonium salt, m.p. 128°-130°

Of compound 181, the di-2-hydroxyethylammonium salt, m.p. 177°-179° (dec)

Of compound 207, the di-2-hydroxyethylammonium salt, m.p. 137°-140°

Of compound 3, the tri-2-hydroxyethylammonium salt, m.p. 154°-158°

Of compound 4, the tri-2-hydroxyethylammonium salt, m.p. 65°-68°

Of compound 30, the tri-2-hydroxyethylammonium salt, m.p. 138°-140°

Of compound 141, the tri-2-hydroxyethylammonium salt, m.p. 140° (gas)

Of compound 3, the diisopropylammonium salt, m.p. 208°-210°

Of compound 4, the diisopropylammonium salt, m.p. 210°-220°

Of compound 3, the 2-(2-hydroxyethoxy)ethylammonium salt, m.p. 159°-167° (dec)

Of compound 4, the 2-(2-hydroxyethoxy)ethylammonium salt, m.p. 116° (softens), 205°-207° (dec)

Of compound 30, the 2-(2-hydroxyethoxy)ethylammonium salt, m.p. 140°-142°

Of compound 31, the 2-(2-hydroxyethoxy)ethylammonium salt, m.p. 79°-82°

Of compound 141, the 2-(2-hydroxyethoxy)ethylammonium salt, m.p. 150°

Of compound 246, the 2-(2-hydroxyethoxy)ethylammonium salt, gummy semisolid

Of compound 251, the 2-(2-hydroxyethoxy)ethylammonium salt, m.p. 89° (decomp)

Of compound 252, the 2-(2-hydroxyethoxy)ethylammonium salt, m.p. 88° (decomp), 218° (gas)

Of compound 3, the dimethylammonium salt, m.p. 155°-180°

Of compound 4, the dimethylammonium salt, m.p. 98°-101°

Of compound 141, the dimethylammonium salt, m.p. 163°-165°

Of compound 142, the dimethylammonium salt, m.p. 230°

Of compound 153, the dimethylammonium salt, m.p. 138°-140° (gas)

Of compound 195, the dimethylammonium salt, m.p. 53°-55°

Of compound 206, the dimethylammonium salt, m.p. 145°-153°

Of compound 3, the octylammonium salt, m.p. 142°–148°

Of compound 4, the octylammonium salt, m.p. 204°–207°

Of compound 30, the octylammonium salt, m.p. 156° (softens), 210°

Of compound 141, the octylammonium salt, m.p. 245°–255°

Of compound 3, the tetradecylammonium salt, m.p. 125°–129°

Of compound 4, the tetradecylammonium salt, m.p. 214°–216°

Of compound 30, the piperidino salt, m.p. 136°

Of compound 267, the 2-(2-hydroxyethoxy)ethylammonium salt, 82°–93° (softens), 170°–200°

Of compound 22, the isopropylammonium salt, m.p. 131°–132° (gas)

Of compound 30, the isopropylammonium salt, m.p. 136° (gas)

Of compound 30, the methylglycinate salt, m.p. 159°–160°.

Of compound 31, the aminopropylmorpholine salt, m.p. 183°–188°

Of compound 3, the aminopropylmorpholine salt, m.p. 74°–77° (softens), 201°–203°

Of compound 4, the aminopropylmorpholine salt, m.p. 91°–94° (softens), 196°–203°

Of compound 30, the aminopropylmorpholine salt, m.p. 190°–195°

(For the structure of compounds 1, 3, 4, 22, 30, 31, 154, 246, 251 and 252 see Table A. For the structure of compound 204, see Table B. For the structure of compounds 141, 142, 179, 184, 185, 186 and 188, see Table E. For the structure of compounds 153 and 195–198, see Table F. For the structure of compound 104, see Example 11. For the structure of compounds 206 and 207, see Example 18.)

EXAMPLE 7

A solution of ethyl 2-methylnicotinate (2.0 g, 12.12 mmol), selenium dioxide (20.0 g, 18.18 mmol) and dioxane (10 ml) is heated at 135° for 4 hours. The reaction mixture is filtered and the filtrate is concentrated and purified by prep. TLC to give ethyl 2-formylnicotinate.

Ethyl 2-formylnicotinate (1.0 g, 5.58 mmol) in 1 ml of ethanol is added to an aqueous solution of lithium hydroxide mono-hydrate (0.28 g, 6.70 mmol) in 3 ml of water. The mixture is stirred at RT for 2 hours, then concentrated under vacuum at RT. The resulting lithium salt of 2-formylnicotinic acid is dissolved in 5 ml of methanol, and 4-phenylsemicarbazide (0.77 g, 5.07 mmol) is added. The mixture is stirred at RT overnight. The resulting white precipitate is filtered and washed with methanol to give the lithium salt of 2-formylnicotinic acid 4-phenylsemicarbazone, m.p. 266°.

Following the above procedure, the lithium salt of 2-acetylnicotinic acid 4-(3-fluorophenyl)semicarbazone, m.p. 208°–209°, is prepared. (Of compound 4, the lithium salt.)

EXAMPLE 8

To a solution of the sodium salt of compound 4 (1.50 g, 4.4 mmol) in 18 ml of methanol is added, with stirring, calcium chloride (0.25 g, 2.2 mmol) in 5 ml of methanol. After ca. 2 hours, the resulting gel-like material is filtered, and the filter pad is washed with water and air-dried to give a white solid which, upon further drying under vacuum at 50° for 3 hours and then at RT overnight, yields the calcium salt of compound 4, m.p. 194°–195°.

A suspension of 1 gm of compound 4 in 15 ml of methanol is treated with a solution of 0.3 gm of magnesium chloride in 3 ml of methanol and the mixture stirred for 3 hrs. The solvent is stripped and the residue dried under high vacuum, m.p. 158°.

EXAMPLE 9

A suspension of 2-acetylnicotinic acid 4-phenylsemicarbazone (compound 1) (0.50 g) in 20 ml of methanol is treated with diazomethane until the yellow color of the solution persists. The solvent is removed in vacuo to give methyl 2-acetylnicotinate 4-phenylsemicarbazone, m.p. 177°–178° (compound 53, Table C).

EXAMPLE 10

A mixture of the sodium salt of compound 4 (1.0 g, 3.0 mmol) and chloromethyl acetate (0.4 g, 3.5 mmol) in 18 ml of DMF is stirred at RT for 3 days. The reaction mixture is poured onto ice. The solid which precipitates is collected by filtration, is washed with water and is air-dried. It is stirred in 50 ml of chloroform for 2 hours and is filtered. The filtrate is evaporated to give glass-like material, which is triturated with ether to give the crude product. Purification by prep. TLC gives acetyloxymethyl 2-acetylnicotinate 4-(3-fluorophenyl)-semicarbazone, m.p. 159°–160° (compound 54, Table C).

Following the above procedure, each of the semicarbazone compounds 55–62, 80–86 and 162–173 in Table C, compounds 190–194, 211, 212, 219, 220, 238 and 239 in Table E and compounds 200–202 in Table F is prepared from the corresponding sodium salt of the semicarbazone carboxylate.

EXAMPLE 11

A mixture of methyl 3-oxo-2-(2-nitrobenzylidenyl)-pentanoate (2.0 g, 7.8 mmol) and iron (2.2 g, 40.0 mmol) in 25 ml of acetic acid is heated at 80° until gas evolution begins. The mixture is allowed to cool to RT and the iron is removed. The mixture is filtered and the filtrate is stripped. The residue is taken up in chloroform, stirred with decolorizing carbon and sodium sulfate and filtered. The solvent is removed by vacuum and the residue is purified by column chromatography to give methyl 2-ethyl-3-quinoline-carboxylate.

A mixture of the above carboxylate (0.22 g, 1.0 mmol) and bromine (0.22 g, 1.4 mmol) in 5 ml of carbon tetrachloride is heated to reflux under floodlamp irradiation and with ca. 5 mg of benzoyl peroxide. After ca. 4 hours, the reaction mixture is cooled to RT and decanted, and the residue is washed with chloroform. The organic layers are combined and the solvent is removed under vacuum to give methyl 2-(1-bromoethyl)-3-quinoline-carboxylate.

A mixture of the above bromide (1.0 mmol) and sodium bicarbonate (0.65 g, 7.7 mmol) in 5 ml of dimethylsulfoxide (DMSO) is quickly heated to 110° and heating is continued for 45 min. The reaction mixture is cooled to RT, diluted with chloroform, washed with water and dried and the solvent is removed in vacuo. The crude product is purified by prep. TLC to give methyl 2-acetyl-3-quinolinecarboxylate.

Following the procedure of Example 30, methyl 2-acetyl-3-quinoline-carboxylate is reacted with lithium hydroxide monohydrate and with hydrochloric acid to give the corresponding acid.

Following the procedure of Example 2, each of 2-acetyl-3-quinoline-carboxylic acid, 3-acetyl-2-quinolinecarboxylic acid and 3-acetyl-4-quinoline-carboxylic acid is reacted with 4-phenylsemicarbazide to give, respectively.

2-acetyl-3-quinolinecarboxylic acid 4-phenylsemicarbazone, m.p. 234°-236° (compound 101);

3-acetyl-2-quinolinecarboxylic acid 4-phenylsemicarbazone, m.p. 243° (gas) (compound 102); and 3-acetyl-4-quinolinecarboxylic acid 4-phenylsemicarbazone, m.p. 251° (dec.) (compound 103).

In the same manner, 3-acetyl-4-quinolinecarboxylic acid is reacted with 4-(3-chlorophenyl)semicarbazide to give 3-acetyl-4-quinolinecarboxylic acid 4-(3-chlorophenyl)semicarbazone, m.p. 229° (compound 104).

EXAMPLE 12

Following the procedure of Example 4, each of compounds 101-104 is reacted with sodium methoxide to give:

the sodium salt of compound 101, m.p. 224°-225° (gas);
the sodium salt of compound 102, m.p. 300°;
the sodium salt of compound 103, m.p. 300°; and
the sodium salt of compound 104, m.p. 300°.

EXAMPLE 13

To a suspension of 2-acetyl-3-nicotinic acid N-oxide (2.5 g, 13.8 mmol) in 40 ml of ethanol is added 4-phenylsemicarbazide (2.1 g, 13.8 mmol). The mixture is stirred at 40° overnight, after which the solvent is removed and the product purified to give 2-acetyl-3-nicotinic acid N-oxide 4-phenyl-semicarbazone, m.p. 218° (dec.) (compound 145).

In the same manner, 2-acetyl-3-nicotinic acid N-oxide (1.5 g, 8.3 mmol) and 2-methyl-4-phenylsemicarbazide are reacted together to give 2-acetyl-3-nicotinic acid N-oxide 2-methyl-4-phenylsemicarbazone, m.p. 55° (softens), 65° (melts) (compound 146).

Following the procedure of Example 4, the sodium salt of 2-acetyl-3-nicotinic acid N-oxide 4-phenyl-semicarbazone is prepared, m.p. 128°-133°. (Of compound 145 the sodium salt.)

Following the procedure of Example 5, the ammonium salt of 2-acetyl-3-nicotinic acid N-oxide 4-phenyl-semicarbazone is prepared, m.p. 137° (softens), 155° (gas). (Of compound 145 the ammonium salt.)

EXAMPLE 14

A mixture of 2-acetylnicotinic acid (1.2 g, 7.3 mmol), oxalyl chloride (1.0 g, 8.0 mmol), DMF (1 drop) in 10 ml of benzene is stirred at RT for 3 hours. The reaction mixture is then decanted and the solvent is removed in vacuo to give the corresponding acid chloride. The acid chloride is taken up in 30 ml of chloroform, and diethylamine (2-3 ml) is added. The mixture is stirred at RT for 1 hour, after which it is stripped. The residue is dissolved in 50 ml of chloroform and washed with water and with sat. sodium chloride. The organic layer is separated and dried and the solvent is removed by rotoevaporation to give N,N-diethyl 2-acetyl-3-nicotinamide.

A mixture of the above nicotinamide (0.45 g, 2.0 mmol) and 4-phenylsemicarbazide (0.31 g, 2.0 mmol) in 10 ml of acetic acid is stirred at RT overnight. The solvent is then removed by rotoevaporation, and the residue is triturated with methanol. The solid is collected by filtration and is dried to give N,N-diethyl 2-acetyl-3-nicotinamide 4-phenylsemicarbazone, m.p. 241°-243° (compound 147).

Following the above procedures, each of 4-(3-fluorophenyl)semicarbazide and 4-(3-chlorophenyl)semicarbazide is reacted with N,N-diethyl 2-acetyl-3-nicotinamide to give N,N-diethyl 2-acetyl-3-nicotinamide 4-(3-fluorophenyl)semicarbazone (compound 148) and N,N-diethyl 2-acetyl-3-nicotinamide 4-(3-chlorophenyl)semicarbazone (compound 149), respectively.

EXAMPLE 15

Following the procedures of Example 14, 2-acetylnicotinic acid chloride (1.0 g, 5.5 mmol) and morpholine (0.6 g, 6.7 mmol) are reacted together to give 4-(2-acetylnicotinyl)morpholine, which compound (1.0 g, 4.2 mmol) is then reacted with 4-(3-fluorophenyl)-semicarbazide (0.7 g, 4.2 mmol) to give 4-(2-acetylnicotinyl)morpholine 4-(3-fluorophenyl)semicarbazone, m.p. 193°-195° (compound 150).

Using thiomorpholine in place of morpholine the following compound may for example be obtained:
4-(2-acetylnicotinyl)thiomorpholine 4-(3-fluorophenyl)semicarbazone, m.p. 206°-208° (compound 269).

EXAMPLE 16

To a mixture of compound 13 (7.35 g, 23.4 mmol) and potassium carbonate (6.5 g, 47.0 mmol) in 50 ml of dimethylformamide is added 2.9 ml (6.67 g, 47.0 mmol) of methyl iodide. The mixture is stirred at RT overnight, and is then poured into ether/CHCl$_3$ and water. The organic phase is separated, washed with sodium bicarbonate and with brine and dried and the solvent is removed to give, following crystallization from CH$_3$CN, the corresponding isothiosemicarbazone (compound 152, Table F) as a mixture of isomers.

To a suspension of the above ester (5.2 g, 15.2 mmol) in 80 ml of methanol is added a solution of lithium hydroxide monohydrate (0.638 g, 15.2 mmol) in 7 ml of water. The suspension is heated to 60° for 7 days, after which the reaction mixture is cooled and the solid is filtered out. The remaining solution is concentrated by rotoevaporation, and conc. HCl and water are added. The resulting solid is collected by vacuum filtration to give compound 151 under Table F.

EXAMPLE 17

To a suspension of compound 14 (15.0 g, 43.1 mmol) in 110 ml of methanol is added sodium methoxide (4.65 g, 86.2 mmol), followed by addition of methyl iodide (6.12 g, 43.1 mmol). The mixture is stirred at RT for 3 hours, after which the solvent is removed by rotoevaporation. The residue is taken up in water and extracted with chloroform. The aqueous fraction is acidified with dilute HCl and extracted with chloroform. This chloroform extract is washed with water and with brine and dried, and the solvent is removed to give compound 153 under Table F.

Following the above procedures, compound 159 is reacted with each of methyl iodide, bromoethane, allyl bromide and benzyl bromide to give, respectively, compounds 195-198 under Table F.

EXAMPLE 18

Following the procedures of Example 17, each of compounds 182 and 183 is reacted with methyl iodide to give, respectively.

3-acetyl-4-isothiazolecarboxylic acid S-methyl-4-(3-chlorophenyl)isothiosemicarbazone, m.p. 149°-153° (compound 206), and 3-acetyl-4-isothiazolecarboxylic acid S-methyl-4-(3-fluorophenyl)isothiosemicarbazone. m.p. 145°-148° (compound 207).

EXAMPLE 19

Following the procedure of Example 4, each of compounds 206 and 207 is reacted with sodium methoxide to give:
the sodium salt of compound 206, m.p. 122°-130°, and the sodium salt of compound 207, m.p. 116°-136°.

EXAMPLE 20

Following the procedure of Example 10, the sodium salt of each of compounds 206 and 207 is reacted with chloromethyl 2,2-dimethylpropanoate to give, respectively, t-butylcarbonyloxymethyl3-acetyl-4-isothiazolecarboxylateS-methyl-4-(3-chlorophenyl)isothiosemicarbazone, viscous yellow oil (compound 208), and t-butylcarbonyloxymethyl3-acetyl-4-isothiazolecarboxylateS-methyl-4-(3-fluorophenyl)isothiosemicarbazone, m.p. 68°-74° (compound 209).

EXAMPLE 21

To 50 mg of 2-acetylnicotinic acid are added 56 mg of 4-(3,5-difluorophenyl)semicarbazide and 1 mL of methanol. After a minute of stirring the product begins precipitating from the solution. After stirring overnight (15 h) the stir vane is removed and rinsed with 0.2 mL of methanol. The reaction mixture is centrifuged and the supernatant solution removed. In the same way the solid is rinsed with methanol (3×0.5 mL) and ether (1×0.5 mL). The solid is dried in vacuo with heating to give 2-acetylnicotinic acid 4-(3,5-difluorophenyl)-semicarbazone (also known as 2-[methyl-{[(3,5-difluorophenylamino)carbonyl]hydrazono}methyl]-3-pyridine-carboxylic acid), m.p. 186° (compound 31, Table A).

To the above acid, suspended in methanol is added one equivalent of 2-(2-aminoethoxy)ethanol. The mixture is stirred for 30 minutes and the solvent then removed by rotoevaporation leaving the 2-(2-hydroxyethoxy)-ethyl ammonium salt of compound 31 as an amorphous solid m.p. 79°-82°.

TABLE A

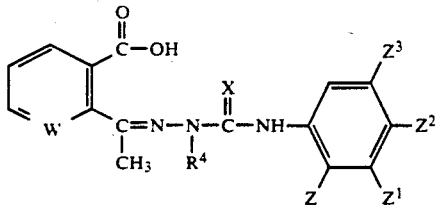

(Formula $A_3$)

| Cpd. No. | W | $R^4$ | X | Z | $Z^1$ | $Z^2$ | $Z^3$ | m.p. acid | Na salt | $NH_4$ salt |
|---|---|---|---|---|---|---|---|---|---|---|
| 1 | N | H | O | H | H | H | H | 174* | 203 | 146# 200* |
| 2 | CH | $CH_3$ | O | H | $CF_3$ | H | H | 172* | 148* | |
| 3 | N | H | O | H | Cl | H | H | 153* | 205* | |
| 4 | N | H | O | H | F | H | H | 159* | 220# 232* | 140# 200* |
| 5 | N | H | O | H | $CF_3$ | H | H | 163-164 | 194* | |
| 6 | N | H | O | H | H | Cl | H | 227* | 213* | |
| 7 | N | H | O | Cl | H | H | H | 300 | 131-132* | |
| 8 | N | H | O | H | Cl | Cl | H | 163* | 189# 201* | |
| 9 | N | H | O | H | $CH_3$ | H | H | 166-167* | 211* | 192# 207* |
| 10 | N | H | O | H | H | F | H | 146-149* 208-220 | 170# 205* | |
| 11 | N | H | O | H | $OCH_3$ | H | H | 162-165* | 197* | |
| 12 | N | H | O | F | H | H | H | 162-165* | 197* | |
| 13 | N | H | S | H | H | — | H | H | 158-160 | |
| 14 | N | H | S | H | Cl | H | H | 108-110* | 108+ | |
| 15 | N | H | S | F | H | H | H | 159-161* | 128-130* | |
| 16 | N | H | S | H | H | F | H | 173-174 | 159-163 | |
| 17 | N | H | S | H | Cl | Cl | H | 169-170 | 121-124* | |
| 18 | N | H | O | H | H | $O-C_6H_5$ | H | 148+ | 211* | |
| 19 | N | $CH_3$ | O | H | H | H | H | 98-100# 140* | 147-56*+ | 140-47 |
| 20 | N | $CH_3$ | O | H | Cl | H | H | 69# 140 | 118* | |
| 21 | N | $CH_3$ | O | H | F | H | H | 120-130 | 120# 140* | |
| 22 | CH | H | O | H | H | H | H | 174 | 184-86* | 150# |
| 23 | CH | H | O | H | $CF_3$ | H | H | 164* | 255 | |
| 24 | CH | H | O | H | Cl | H | H | 158* | 126* | 87# 140-147 |
| 25 | CH | H | O | H | F | H | H | 169* | 203* | |
| 26 | CH | H | O | H | $CF_3$ | Cl | H | 170* | 173* | |
| 27 | CH | H | S | H | H | H | H | 129-131 | 115# 134* | |

TABLE A-continued

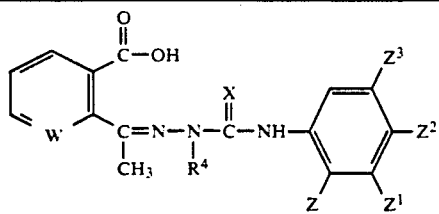

(Formula A₃)

| Cpd. No. | W | R⁴ | X | Z | Z¹ | Z² | Z³ | m.p. acid | Na salt | NH₄ salt |
|---|---|---|---|---|---|---|---|---|---|---|
| 28 | CH | CH₃ | O | H | H | H | H | 177 | | |
| 29 | CH | CH₃ | O | H | H | CH₃ | H | 176–178* | | |
| 30 | N | H | O | H | Cl | H | Cl | 193+ | 222* | |
| 31 | N | H | O | H | F | H | F | 186* | 240* | |
| 32 | N | H | O | F | F | H | H | 168# 202 | 220* | |
| 33 | N | H | O | Cl | Cl | H | H | 168# 198 | 194* | |
| 34 | N | H | O | F | H | H | F | 154–157 | 234–235* | |
| 35 | N | H | O | F | H | H | CH₃ | 173# 203 | 226–227* | |
| 36 | N | H | O | H | OCH₃ | H | OCH₃ | 185* | 203 | |
| 37 | N | H | O | F | H | H | Cl | 167–171* | 204–206+ | |
| 38 | N | H | O | F | Cl | H | H | 152–154* | 200–202+ | |
| 39 | N | H | O | H | Cl | Cl | H | 163* | 189# | |
| 40 | N | H | O | H | NO₂ | H | H | 190+ | 194–195+ | |
| 41 | N | H | S | H | CN | H | H | 168–169 | 166# | |
| 42 | N | H | O | H | Br | H | H | 175* | 208–210* | |
| 43 | N | H | O | H | I | H | H | 174* | 212* | |
| 44 | N | H | O | H | OH | H | H | 204–210 | | |
| 45 | N | H | O | H | OC₆H₅ | H | H | 164* | 206* | |
| 46 | N | H | O | H | C₂H₅ | H | H | 178–180* | 200# | |
| 47 | N | H | O | H | OnC₄H₉ | H | H | 172–175* | 207* | |
| 154 | CH | H | O | H | Cl | H | Cl | 185–186 | 199–200 | |
| 155 | N | H | O | H | CH₃ | H | CH₃ | 198# 228 | 228* | |
| 156 | N | H | O | H | C(CH₃)=CH₂ | H | H | 171–173 | 213+ | |
| 157 | N | H | O | H | Br | H | Br | 202* | | |
| 158 | N | H | S | H | CH₃ | H | H | 177 | 198–201* | |
| 159 | N | H | S | H | F | H | H | 168–169* | 170–173 | |
| 160 | N | H | O | H | SCH₃ | H | H | 174–175* | 208–209 | |
| 161 | N | H | O | H | OCF₃ | H | H | 191–192* | 225–227 | |
| 217 | N | H | O | H | OCHF₂ | H | H | 193* | 208–212 | |
| 218 | N | H | O | H | OCF₂CHF₂ | H | H | 157# 188 | 182 | |
| 240 | N | CH₂CH₂OH | O | H | F | H | H | 146–148* | 80–83* | |
| 241 | N | H | O | H | H | CH₃ | H | 218 | 208* | |
| 242 | N | H | O | OCH₃ | H | H | H | 148–150 | 198–202 | |
| 243 | N | H | O | H | CH₃ | F | H | 222–230 | 220* | |
| 244 | CH | H | O | H | F | H | F | 179* | 187* | |
| 245 | N | H | O | H | H | I | F | | 195* | |
| 246 | N | CH₃ | O | H | F | H | F | 145–146* | 140# 160* | |
| 247 | N | H | O | H | F | F | H | 172 | 203* | |
| 248 | N | H | F | F | H | F | H | 205 | 215+ | |
| 249 | N | H | O | H | Cl | F | H | 155* | 199* | |
| 250 | N | H | O | H | Cl | Cl | Cl | 235+ | | |
| 251 | N↓O | H | O | H | F | H | H | 220* | 202* | |
| 252 | N↓O | H | O | H | F | H | F | 220* | >220 | |
| 256 | CH | H | O | H | H | Cl | H | | 208–209* | |
| 266 | N | H | O | H | N₃ | H | H | 173–4** | 229–233** | |
| 267 | N | H | O | H | F | H | Cl | 177–8* | 214* | |

TABLE B (Formula A₄)

Structure: Pyridine with COOH, W, and C(CH₃)(R⁴)=N—N—CO—NH—R¹⁰

| Cpd. No. | W | R⁴ | R¹⁰ | m.p. Acid | Na-salt |
|---|---|---|---|---|---|
| 48 | N | H | 2-pyridyl | 195–197 | 183 |
| 49 | N | H | 6-chloro-2-pyridyl | 171–172 | 190–194 |
| 50 | N | H | 3-pyridyl | 167#, 206–208 | 208* |
| 51 | CH | H | 2-pyridyl | 128–129* | 200* |
| 52 | CH | H | 3-pyridyl | 152–153 | 175+ |
| 203 | N | H | 3-chloro-4-pyridyl | 187–188 | 201–203+ |
| 204 | N | H | 5-methyl-2-(1,3,4-thiadiazole) | 256–258 | 242–244 |
| 205 | N | H | 2-thiazole | 164#, 235+ | 219* |
| 210 | N | H | 5-ethyl-2-(1,3,4-thiadiazole) | 240–244* | 232–235* |
| 257 | CH | CH₃ | 1-naphthyl | 168–169* | |

TABLE C (Formula A₅)

Structure: Pyridine with Y, Y¹, Y², C(=O)OR⁵, and C(CH₃)=N—NH—C(=O)—NH—phenyl(Z¹,Z³)

| Cpd | Y | Y¹ | Y² | R⁵ | Z¹ | Z³ | m.p. acid/ester | Na salt |
|---|---|---|---|---|---|---|---|---|
| 53 | H | H | H | CH₃ | H | H | 177–178 | — |
| 54 | H | H | H | CH₂—O—C(O)—CH₃ | F | H | 159–160 | — |
| 55 | H | H | H | CH₂—O—C(O)—CH₂CH₂CH₃ | F | H | 108–124 | — |
| 56 | H | H | H | CH(CH₃)—O—C(O)—CH₂—CH₃ | F | H | 158–164 | — |
| 57 | H | H | H | CH(CH₃CHCH₂CH₃)—O—C(O)—CH₃ | F | H | 182–186 | — |
| 58 | H | H | H | CH₃ | F | H | 206–214 | — |
| 59 | H | H | H | CH₂—O—C(O)—CH₃ | Cl | H | 148–150 | — |
| 60 | H | H | H | CH(CH₃)—O—C(O)—CH₂CH₃ | Cl | H | 168–170 | — |
| 61 | H | H | H | CH₂—O—C(O)—CH₂CH₂CH₃ | Cl | H | 150–152 | — |
| 62 | H | H | H | CH₂—O—C(O)—(CH₂)₆CH₃ | Cl | H | 46–47 | — |
| 63 | OCH₃ | H | H | H | F | H | 220–240 | 208* |
| 64 | Cl | H | H | H | H | H | 225 | |
| 65 | Cl | H | H | H | F | H | 210–214* | 200+ |
| 66 | H | OCH₂CH₃ | H | H | H | H | 141–142 | |
| 67 | H | OCH₂CH₃ | H | H | F | H | 135–136 | 233–235 |
| 68 | H | Cl | H | H | Cl | H | 163–164 | >330 |
| 69 | H | Cl | H | H | F | H | 157–159 | >320 |
| 70 | H | C₆H₅ | H | H | H | H | 193–195 | 242–244+ |
| 71 | H | C₆H₅ | H | H | F | H | 240–250 | 246–248+ |
| 72 | H | H | Cl | H | H | H | | |
| 73 | H | H | Cl | H | F | H | 214–215+ | >320 |
| 74 | H | C₂H₅ | H | H | F | H | 178* | 190–193* |
| 75 | H | CH₃ | H | H | F | H | 167–169* | 228–230* |
| 76 | CH₃ | H | H | H | F | H | 186–188 | 214–216 |
| 77 | C₂H₅ | H | H | H | F | H | 160–161 | 233–235 |
| 78 | H | H | CH₃ | H | F | H | | |
| 79 | H | H | C₂H₅ | H | F | H | | |

TABLE C-continued (Formula A₅)

| Cpd | Y | Y¹ | Y² | R⁵ | Z¹ | Z³ | m.p. (°C.) acid/ester | Na salt |
|---|---|---|---|---|---|---|---|---|
| 80 | OCH₃ | H | H | CH₂—O—CO—CH₂CH₂CH₃ | F | H | — | |
| 81 | Cl | H | H | CH₂—O—CO—CH₂CH₂CH₃ | F | H | 118–120 | — |
| 82 | H | OCH₂CH₃ | H | CH₂—O—CO—CH₂CH₂CH₃ | F | H | 150–152 | — |
| 83 | H | Cl | H | CH₂—O—CO—CH₂CH₃CH₃ | F | H | 160–163 | — |
| 84 | H | C₆H₅ | H | CH₂—O—CO—CH₂CH₂CH₃ | F | H | 197–198 | — |
| 85 | H | H | H | CH₂—O—CO—C(CH₃)₃ | F | H | 173–175* | — |
| 86 | H | H | H | CH₂—O—CO—nC₃H₇ | C₂H₅ | H | 103–105* | — |
| 162 | H | H | H | CH₂—O—CO—CH₂CH₂CH₃ | Cl | Cl | 187–190 | — |
| 163 | H | H | H | CH₂—O—CO—C(CH₃)₃ | S—CH₃ | H | 133–134 | — |
| 164 | H | H | H | CH₂—O—CO—C(CH₃)₃ | Cl | Cl | 189–190 | — |
| 165 | H | H | H | CH(CH₃)—O—CO—CH(CH₂CH₃)(CH₂)₃CH₃ | F | H | 85–103 | — |
| 166 | H | H | H | CH(CH₃)—O—CO—CH₂CH(CH₃)₂ | F | H | 137–150 | — |
| 167 | H | H | H | CH(CH₃)—O—CO—(CH₂)₄CH₃ | F | H | 138–148 | — |
| 168 | H | H | H | CH(CH₃)—O—CO—CH(CH₃)CH₂CH₃ | F | H | 149–150 | — |
| 169 | H | H | H | CH(CH₃)—O—CO—C(CH₃)₃ | F | H | 168–170 | — |
| 170 | H | H | H | CH(CH₃)—O—CO—CH₂CH₂CH₃ | F | H | 160–161 | — |
| 171 | H | H | H | CH(CH₂CH₃)—O—CO—CH₂CH₂CH₃ | F | H | | — |

TABLE C-continued (Formula A₅)

| Cpd | Y | Y¹ | Y² | R⁵ | Z¹ | Z³ | m.p. (°C.) acid/ester | Na salt |
|---|---|---|---|---|---|---|---|---|
| 172 | H | H | H | CH₂—O—C(=O)—C(CH₃)₃ | Cl | H | 173–177 | — |
| 173 | H | H | H | CH₂—O—C(=O)—C(CH₃)₃ | F | F | 191–192 | — |
| 268 | OH | H | H | H | H | H | >300 | >300 |

TABLE D (Formula A₆)

| Cpd. No. | W | W' | W''' | W'''' | Z¹ | m.p. acid | Na salt |
|---|---|---|---|---|---|---|---|
| 87 | CH | CH | CH | N | H | 160–162+ | |
| 88 | CH | CH | CH | N | F | 125–133* | 198–199+ |
| 89 | CH | N | CH | CH | H | 230–245 | |
| 90 | CH | N | CH | CH | F | | |
| 91 | CH | CH | N | CH | H | 180–182+ | |
| 92 | CH | CH | N | CH | F | | |
| 93 | CH | N | C—Cl | N | H | 165–167 | 230–240* |
| 94 | CH | N | C—Cl | N | F | | |

TABLE D-continued (Formula A₆)

| Cpd. No. | W | W' | W''' | W'''' | Z¹ | m.p. acid | Na salt |
|---|---|---|---|---|---|---|---|
| 95 | CH | N | CH | N | H | 194–195* | 214–216* |
| 96 | CH | N | CH | N | F | | |
| 97 | N | CH | N | CH | H | 196–198* | 207–208+ |
| 98 | N | CH | N | CH | F | | |
| 99 | N | CH | CH | N | H | 164–169+ | |
| 100 | N | CH | CH | N | F | | |

TABLE E (Formula A₇)

| Cpd | Q' | Q'' | Q''' | R³ | R⁵ | X | Z | Z¹ | Z² | Z³ | m.p. acid | Na salt |
|---|---|---|---|---|---|---|---|---|---|---|---|---|
| 105 | CH | S | CH | CH₃ | H | O | H | H | H | H | 238 | 270 |
| 106 | CH | S | CH | CH₃ | H | O | Cl | H | H | H | 235 | >290 |
| 107 | CH | S | CH | CH₃ | H | O | H | Cl | H | H | 258 | |
| 108 | CH | S | CH | CH₃ | H | O | H | H | Cl | H | 240 | 203 |
| 109 | CH | S | CH | CH₃ | H | O | H | Cl | H | Cl | 210 | 240–244 |
| 110 | CH | S | CH | CH₃ | H | O | H | F | H | H | 252 | 222 |
| 111 | CH | S | CH | CH₃ | H | O | H | H | F | H | 260 | 280 |
| 112 | CH | S | CH | CH₃ | H | O | H | OCH₃ | H | H | 262 | 280 |
| 113 | CH | CH | S | CH₃ | H | O | H | H | H | H | 258 | 223 |
| 114 | CH | CH | S | CH₃ | H | O | Cl | H | H | H | 256 | 201–209 |
| 115 | CH | CH | S | CH₃ | H | O | H | Cl | H | H | 249 | 192–203 |
| 116 | CH | CH | S | CH₃ | H | O | H | H | Cl | H | 251 | 242 |
| 117 | CH | CH | S | CH₃ | H | O | H | Cl | H | Cl | 216 | 242–246 |
| 118 | CH | CH | S | CH₃ | H | O | H | F | H | H | 255 | 239– |

TABLE E-continued (Formula A₇)

$$\underset{R^3}{\overset{Q'''}{\underset{Q''}{\overset{Q'}{\bigcirc}}}}\overset{COOR^5}{\underset{C=N-NH-\overset{X}{\underset{}{C}}-NH}{}}\underset{Z}{\overset{Z^3}{\bigcirc}}\underset{Z^1}{Z^2}$$

| Cpd | Q' | Q'' | Q''' | R³ | R⁵ | X | Z | Z¹ | Z² | Z³ | m.p.° | Na salt |
|---|---|---|---|---|---|---|---|---|---|---|---|---|
| 119 | CH | CH | S | CH₃ | H | O | H | H | F | H | 261 | 235–239 |
| 120 | CH | CH | S | CH₃ | H | O | H | OCH₃ | H | H | 253 | 225 |
| 121 | S | CH | CH | CH₃ | H | O | H | H | H | H | 170–171 | 232–233 |
| 122 | S | CH | CH | CH₃ | H | O | H | Cl | H | H | 174–175 | 223–224 |
| 123 | S | CH | CH | CH₃ | H | O | H | Cl | H | Cl | 207–208 | 210+ |
| 124 | S | CH | CH | CH₃ | H | O | H | F | H | H | 174–176 | 218–220 |
| 125 | S | CH | CH | CH₃ | H | O | H | F | H | F | 194–195 | 227–229 |
| 126 | CH | O | CH | CH₃ | H | O | H | H | H | H | 240 | 210+ |
| 127 | CH | O | CH | CH₃ | H | O | H | Cl | H | H | 256 | 235+ |
| 128 | CH | O | CH | CH₃ | H | O | H | Cl | H | Cl | | |
| 129 | CH | O | CH | CH₃ | H | O | H | F | H | H | 253 | 225+ |
| 130 | CH | O | CH | CH₃ | H | O | H | F | H | F | | |
| 131 | CH | CH | O | CH₃ | H | O | H | H | H | H | | |
| 132 | CH | CH | O | CH₃ | H | O | H | Cl | H | H | | |
| 133 | CH | CH | O | CH₃ | H | O | H | Cl | H | Cl | | |
| 134 | CH | CH | O | CH₃ | H | O | H | F | H | H | | |
| 135 | CH | CH | O | CH₃ | H | O | H | F | H | F | | |
| 136 | O | CH | CH | CH₃ | H | O | H | H | H | H | | |
| 137 | O | CH | CH | CH₃ | H | O | H | Cl | H | H | | |
| 138 | O | CH | CH | CH₃ | H | O | H | Cl | H | Cl | | |
| 139 | O | CH | CH | CH₃ | H | O | H | F | H | H | | |
| 140 | O | CH | CH | CH₃ | H | O | H | F | H | F | | |
| 141 | S | N | CH | CH₃ | H | O | H | F | H | H | 222+ | 202–205* |
| 142 | S | N | CH | CH₃ | H | O | H | Cl | H | H | 244–247 | 200–206* |
| 143 | CH | N | S | CH₃ | H | O | H | F | H | H | 208–210 | 268–278 |
| 144 | CH | N | S | CH₃ | H | O | H | Cl | H | H | | |
| 174 | CH | S | N | CH₃ | H | O | H | F | H | H | 187–189 | 236–240+ |
| 175 | N | N | S | CH₃ | H | O | H | F | H | H | 205–207+ | 220–230+ |
| 176 | CH | N | O | CH₃ | H | O | H | F | H | H | 238–240+ | 265–290+ |
| 177 | C—NO₂ | S | CH | CH₃ | H | O | H | H | H | H | 200*+ | |
| 178 | C—NO₂ | S | CH | CH₃ | H | O | H | F | H | H | 205*+ | |
| 179 | S | N | CH | CH₃ | H | O | H | H | H | H | 199–204 | 199# |
| 180 | S | N | CH | CH₃ | H | O | H | Cl | H | Cl | 235–237+ | 198 |
| 181 | S | N | CH | CH₃ | H | O | H | F | H | F | 241–243+ | 238–239+ |
| 182 | S | N | CH | CH₃ | H | S | H | Cl | H | H | 188–189+ | 167–172+ |
| 183 | S | N | CH | CH₃ | H | S | H | F | H | H | 189–196+ | 164–169+ |
| | | | | | | | | | | | acid/ester | |
| 184 | S | N | CH | CH₃ | H | O | H | CH₃ | H | H | 208#, 255* | 204–208* |
| 185 | S | N | CH | CH₃ | H | O | H | CH₂CH₃ | H | H | 201#, 260* | 198–201* |
| 186 | S | N | CH | CH₃ | H | O | H | Br | H | H | | 197–204+ |
| 187 | S | N | CH | CH₃ | H | O | H | I | H | H | | 199–205+ |
| 188 | S | N | CH | CH₂CH₃ | H | O | H | F | H | H | 182–183 | 179–183 |
| 189 | S | N | CH | CH₂CH₃ | H | O | H | Cl | H | H | 178–183 | 172–178* |
| 190 | S | N | CH | CH₃ | CHOCCH(CH₂)₃CH₃ ‖ O ∣ ∣ CH₃ CH₂CH₃ | O | H | F | H | H | | — |

TABLE E-continued

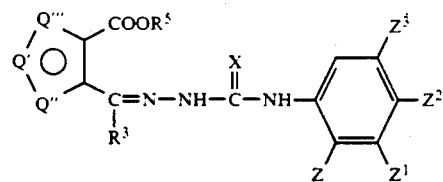
(Formula A₇)

| Cpd | Q' | Q" | Q''' | $R^3$ | $R^5$ | X | Z | $Z^1$ | $Z^2$ | $Z^3$ | m.p.° | Na salt |
|---|---|---|---|---|---|---|---|---|---|---|---|---|
| 191 | S | N | CH | $CH_3$ | $CH_2OCC(CH_3)_3$ (=O) | O | H | H | H | H | 163-171 | — |
| 192 | S | N | CH | $CH_3$ | $CH_2OCC(CH_3)_3$ (=O) | O | H | F | H | H | 159-169 | — |
| 193 | S | N | CH | $CH_3$ | $CH_2OCC(CH_3)_3$ (=O) | O | H | Cl | H | H | 155-165 | — |
| 194 | S | N | CH | $CH_3$ | $CH_2OCC(CH_3)_3$ (=O) | O | H | Cl | H | Cl | 183-194 | — |
| 211 | S | N | CH | $CH_3$ | $C_6H_5$ | O | H | F | H | H | | |
| 212 | S | N | CH | $CH_3$ | $CH_2CF_3$ | O | H | F | H | H | 200-201 | |
| 213 | S | N | CH | $CH_3$ | H | O | H | $OCHF_2$ | H | H | | |
| 214 | S | N | CH | $CH_3$ | H | O | H | $OCF_3$ | H | H | | |
| 215 | S | N | CH | $CH_3$ | H | O | H | $OCF_2CHF_2$ | H | H | 206* | 214* |
| 216 | CH | O | N | $CH_3$ | H | O | H | F | H | H | 252-253+ | |
| 219 | S | N | CH | $CH_3$ | $CHOCC(CH_3)_3$ (=O), $CH_3$ | O | H | F | H | H | | |
| 220 | S | N | CH | $CH_3$ | $CHOCCHCH_2CH_3$ (=O), $CH_3$, $CH_3$ | O | H | F | H | H | | |
| 221 | N | $N-CH_3$ | CH | $CH_3$ | H | O | H | F | H | H | 290-293+ | 250-260+ |
| 222 | S | N | CH | $CH_3$ | H | O | H | $OCF_3$ | H | H | 218* | 223* |
| 223 | S | N | CH | $CH_3$ | H | O | H | $OCHF_2$ | H | H | 204* | 215* |
| 224 | S | N | CH | $CH_3$ | H | O | H | H | F | H | 243* | 195-201* |
| 225 | S | N | CH | $CH_3$ | H | O | Cl | H | H | H | 218* | 208-212 |
| 226 | S | N | CH | $CH_3$ | H | O | H | H | Cl | H | 249-253* | 203-209 |
| 227 | S | N | CH | $CH_3$ | H | O | H | H | $CH_3$ | H | 237-239 | 216-226+ |
| 228 | S | N | CH | $CH_3$ | H | O | H | $OCH_3$ | H | H | 199* | 208-210 |
| 229 | S | N | CH | $CH_3$ | H | O | $CH_3$ | H | H | H | 276-278 | 194-200 |
| 230 | S | N | CH | $CH_3$ | H | O | H | H | $OCH_3$ | H | 195* | 193-203 |
| 231 | S | N | CH | $CH_3$ | H | O | $OCH_3$ | H | H | H | 214* | 221* |
| 232 | S | N | CH | $CH_3$ | H | O | F | H | H | H | 216* | 246* |
| 233 | S | N | CH | $CH_3$ | H | O | H | H | $CH_3$ | F | H | 222* | 206-220* |
| 234 | S | N | CH | $CH_3$ | H | O | H | $CF_3$ | H | H | 276 | 234-235 |
| 235 | S | N | $C-CH_3$ | $CH_3$ | H | O | H | F | H | H | 189-192* | 255 |
| 236 | S | N | $C-Cl$ | $CH_3$ | H | O | H | F | H | H | 209-210* | 260-268 |
| 237 | S | N | $C-OCH_3$ | $CH_3$ | H | O | H | F | H | H | | 193-195* |
| 238 | S | N | CH | $CH_3$ | $CH_2CF_3$ | O | H | Cl | H | H | 178-182 | — |
| 239 | S | N | CH | $CH_3$ | $C_6H_5$ | O | H | Cl | H | H | 206-208 | — |
| 253 | S | N | CH | $CH_3$ | $CH_3$ | O | H | F | H | H | 178* | — |
| 261 | CH | S | CH | $CH_3$ | $CH_3$ | O | H | F | H | H | 190-193 | |

TABLE F

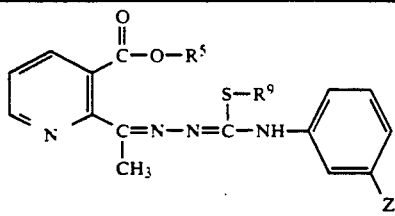
(formula A₈)

| Cpd. No. | R⁵ | R⁹ | Z¹ | m.p.° | Na salt | NH₄ salt |
|---|---|---|---|---|---|---|
| 151 | H | CH₃ | H | 140-142* | 110-120# 140* | |
| 152 | CH₃ | CH₃ | H | 156-159 | — | — |
| 153 | H | CH₃ | Cl | 70# 100-110* | 108#, 134* | |
| 195 | H | CH₃ | F | 80-83 | 155+ | 87-90 |
| 196 | H | CH₂CH₃ | F | 71-73 | 140-143 | |
| 197 | H | CH₂CH=CH₂ | F | 126-127 | 157-160 | |
| 198 | H | CH₂—C₆H₅ | F | 158-159 | 115-117 | |
| 199 | H | CH₃ | CH₃ | 88+ | 64#, 119 | |
| 200 | CH₂OC(O)C(CH₃)₃ | CH₃ | H | 75-78# | — | — |
| 201 | CH₂OC(O)C(CH₃)₃ | CH₃ | Cl | (viscous yellow oil) | — | — |
| 202 | CH₂OC(O)C(CH₃)₃ | CH₃ | F | (oil) | — | — |

TABLE G

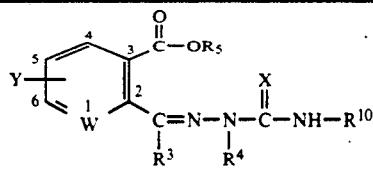

| Cpd. No. | W | Y | R³ | R⁴ | X | R¹⁰ | R⁵ | m.p.° | |
|---|---|---|---|---|---|---|---|---|---|
| 254 | CH | H | CH₃ | H | O | phenyl | CH₃ | 160-162 | |
| 255 | CH | H | C₂H₅ | H | O | phenyl | H | 148-149* | (acid) |
| 258 | N | H | H | CH₃ | O | phenyl | H | 232-235* | (acid) |
| 259 | N | H | CH₃ | H | O | 2,6-difluorophenyl | H | 228* 204* | (acid) (Na⁺ salt) |
| 260 | N | 5-NO₂ | CH₃ | H | O | 3-fluorophenyl | H | 189-191* 189-190.5* | (acid) (Na⁺ salt) |

TABLE H

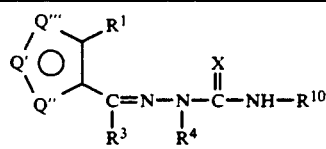

| Cpd. No. | Q' | Q" | Q''' | R³ | R⁴ | R¹ | X | R¹⁰ | m.p.° |
|---|---|---|---|---|---|---|---|---|---|
| 262 | S | N | CH | CH₃ | H | —C(O)—SC₂H₅ | O | 3-chlorophenyl | 144-153 (melts, resolidifies) |
| 263 | S | N | CH | CH₃ | H | —C(O)—SC₂H₅ | O | 3-fluorophenyl | 145-150 (melts, resolidifies) |
| 264 | S | N | CH | CH₃ | H | —C(O)—SC₂H₅ | S | 3-chlorophenyl | 110-124 |
| 265 | S | N | CH | H | CH₃ | —COOH | O | 3-fluorophenyl | 223-225* (acid) 265-270+ (Na⁺ salt) |

INTERMEDIATE COMPOUNDS

EXAMPLE 21

A solution of 3-fluorophenyl isocyanate (5.0 g, 36.0 mmol) in 20 ml of toluene is added to hydrazine hydrate (2.1 g, 42.0 mmol) in 70 ml of dioxane, maintaining the temperature of the reaction at less than 12°. After 2 hours, the reaction is filtered and the solvent is removed from the filtrate by rotoevaporation to give the white solid, 4-(3-fluorophenyl)-semicarbazide.

Following the above procedure, each of 4-phenylsemicarbazide, 4-(3-chlorophenyl)semicarbazide and 4-(3-methylphenyl)semicarbazide is prepared from the corresponding isocyanate and hydrazine hydrate.

EXAMPLE 22

To a solution of 2-fluoroaniline (11.1 g, 100.0 mmol) in 100 ml of dry ether cooled in an ice bath is added ethyl chloroformate (7.1 ml, 8.1 g, 75.0 mmol). After addition, the mixture is allowed to warm to RT and is stirred at RT for 3 hours. Then a 10% sodium hydroxide solution (54 ml, 2.8M, 150.0 mmol) is added, followed by another 7.1 ml of ethyl chloroformate. The mixture is stirred at RT for 3 hours, and is then poured into water and ether. The organic layer is separated, washed with 5% HCl and with brine, and dried. The solvent is removed to give ethyl N-(2-fluorophenyl)carbamate.

A mixture of ethyl N-(2-fluorophenyl)carbamate (8.3 g, 45.4 mmol) and hydrazine hydrate (13.6 g, ca. 14 ml) in 40 ml of absolute ethanol is heated to reflux. After 3 days, the reaction mixture is concentrated, and the solid is filtered, washed with water and with ether and dried to give 4-(2-fluoro-phenyl)semicarbazide.

Following the above procedures, each of 4-(3,5-dichlorophenyl)semicarbazide, 4-(3,5-difluorophenyl)-semicarbazide, 4-(2-pyridyl)semicarbazide and 4-(3-pyridyl)semicarbazide is prepared from hydrazine hydrate and the corresponding substituted carbamate.

EXAMPLE 23

A mixture of 3-chloro-2-methylphenylurea (5.0 g, 27.0 mmol), hydrazine hydrate (4.0 g, 80.0 mmol), 4 ml of water and 30 ml of ethanol is heated to reflux for 12 hours. The reaction mixture is then cooled and poured onto ice. A white precipitate forms, which is collected by filtration, washed with water and dried. The resulting solid is dissolved in hot ethanol and conc. HCl is added. The mixture is cooled and the resulting white solid precipitate is collected by filtration, washed with ethanol, and dried under vacuum to give 4-(3-chloro-2-methylphenyl)semicarbazide hydrochloride.

EXAMPLE 24

Sixteen grams (88.4 mmol) of 2-acetylnicotinic acid N-oxide (J. Chem. Soc., 1961, 5216) is added to a solution of sodium hydroxide (3.5 g, 88.4 mmol) in 300 ml of water. The pH is adjusted to 9 by the addition of 6N NaOH, and 10% palladium on carbon (1.6 g) is added. The mixture is then hydrogenated until a 20% excess of hydrogen is taken up. The reaction mixture is filtered through Celite, and the pH of the filtrate is adjusted to 2.5 with 6N HCL. The solvent is removed by rotoevaporation and the residue is taken up in methanol. The mixture is filtered and the filtrate is evaporated to give a pale beige solid, 2-acetylnicotinic acid.

EXAMPLE 25

An ethereal solution of diazomethane (excess) is added to a stirred suspension of ethyl 1,6-dihydro-2-acetyl-6-oxonicotinate (2.20 g, 10.5 mmol) in 10 ml of ether. The ether and excess diazomethane are removed under vacuum, and the crude product is purified by column chromatography, eluting with 30% ethyl acetate/hexane to give ethyl 2-acetyl-6-methoxynicotinate.

Ethyl 2-acetyl-6-methoxynicotinate (0.92 g, 4.13 mmol) in 20 ml of methanol is stirred with lithium hydroxide monohydrate (0.18 g, 4.20 mmol) in 3 ml of water. After 1.5 hours, the water and methanol are removed by rotoevaporation. The residue is dissolved in chloroform and 3N hydrochloric acid. The aqueous phase is extracted with chloroform and the combined organic extracts are washed with brine and dried and the solvent is removed to give 2-acetyl-6-ωethoxynicotinic acid.

EXAMPLE 26

To sodium balls (4.78 g, 208.0 mmol) under $N_2$ is added 65 ml of ethanol at a rate to maintain reflux and with stirring. To this solution of sodium ethoxide in ethanol is added ethyl propionylacetate (30.0 g, 208.0 mmol) in 30 ml of ethanol. After 30 min., 3-bromopropionitrile (9.38 g, 70.0 mmol) is added dropwise, and the reaction mixture is stirred at RT overnight. The resulting solid is removed by vacuum filtration. Excess ethanol is removed by rotoevaporation, and the residue is poured into ether and 5% hydrochloric acid. The organic phase is separated, washed to neutrality with brine and dried and the solvent is removed to give, after distillation, ethyl 2-(2-cyanoethyl)propionylacetate.

To a well-stirred solution of 8 ml of conc. hydrochloric acid cooled in an ice bath is added the above propionylacetate (6.7 g, 34.0 mmol). The bath is removed after 30 min., and the reaction mixture is warmed to ca. 25°. The mixture is stirred for another 1.5 hours and then poured onto ice. The solid is separated by vacuum filtration and dried overnight to give ethyl 1,4,5,6-tetrahydro-2-ethyl-6-oxonicotinate.

A mixture of the above oxonicotinate (2.7 g, 13.7 mmol) and 2,3-dichloro-5,6-dicyanobenzoquinone (DDQ) in 100 ml of dioxane is heated to reflux overnight, after which the dioxane is removed by rotoevaporation. The residue is dissolved in chloroform and extracted with sat. sodium bicarbonate. The organic fraction is washed with brine and dried and the solvent is removed. The resulting solid is triturated with small volumes of ether/hexane. The solid left undissolved is dried to give ethyl 1,6-dihydro-2-ethyl-6-oxonicotinate.

A mixture of the above 1,6-dihydrooxonicotinate (1.33 g, 6.82 mmol) and phosphorus oxychloride (1.83 ml, 3.06 g, 20.0 mmol) is heated to 120° for 3.5 hours. The reaction mixture is poured onto ice and extracted with chloroform. The combined organic phases are washed with brine and dried and the solvent is removed to give, after purification by column chromatography, ethyl 6-chloro-2-ethylnicotinate.

A solution of ethyl 6-chloro-2-ethylnicotinate (1.0 g, 4.7 mmol), N-bromosuccinimide (0.85 g, 4.8 mmol) and benzoyl peroxide (10 mg) in 10 ml of carbon tetrachloride is heated to reflux while irradiated with a floodlamp for 3 hours. The reaction mixture is cooled and the solid succinimide is removed by filtration. The solid is washed several times with carbon tetrachloride and the filtrate is stripped by rotoevaporation to give ethyl 6-chloro-2-(1-bromoethyl)nicotinate.

Sodium bicarbonate (0.42 g, 5.0 mmol) is added to the above bromide (1.33 g, 4.55 mmol) in 13 ml of dry DMSO. The mixture is heated at 90° for 1.75 hours, then cooled, worked up and dried. The solvent is removed and the crude product is purified by prep. TLC to give ethyl 2-acetyl-6-chloronicotinate. Following the procedure of Example 11, the ethyl 2-acetyl-6- chloronicotinate is reacted with lithium hydroxide monohydrate to give 2-acetyl-6-chloronicotinic acid.

EXAMPLE 27

2-Ethoxy-1-dimethylamino-3-dimethylimonio-1-propene perchlorate (2.00 g, 3.56 mmol) is dissolved in 10 ml of DMF, and ethyl propionylacetate (0.56 g, 3.90 mmol) and potassium carbonate (0.50 g, 3.56 mmol) are added. The reaction mixture is heated at 85°–90° for 1 hour, then cooled to RT. A mixture of 5 ml of ammonium hydroxide in 15 ml of ethanol is added and the reaction is stirred at RT for 2 hours. The resulting mixture is poured onto water and extracted with ethyl acetate, dried and concentrated to give, after purification by flash chromatography, ethyl 5-ethoxy-2-ethylnicotinate. Following the procedure of Example 12, the above nicotinate is brominated by reaction with N-bromosuccinimide, and the resulting bromide is reacted with sodium bicarbonate in DMSO to give ethyl 2-acetyl-5-ethoxy-nicotinate.

Following the procedure of Example 25, the above nicotinate is hydrolyzed to 2-acetyl-5-ethoxynicotinic acid.

EXAMPLE 28

Ammonia is bubbled into a solution of 2-ethyl-3-methoxycarbonyl-4-pyranone (6.5 g) in 70 ml of ethanol, cooled in an acetone/ice bath, for 1 hour. The resulting solution is then heated to reflux for 1.5 hours, cooled and concentrated to give ethyl 1,4-dihydro-2-ethyl-4-oxonicotinate.

A mixture of the above oxonicotinate (6.6 g) and phosphoryl chloride (50 ml) is heated at 120° for 2 hours, then poured onto ice, and diluted and extracted with ethyl acetate. The aqueous layer is cooled to below 50° and treated with 50% sodium hydroxide to pH 7. After cooling to 25°, it is extracted with ethyl acetate. The combined organic layers are dried, concentrated and purified by flash chromatography to give ethyl 4-chloro-2-ethylnicotinate.

A mixture of the above ethylnicotinate (5.45 g), N-bromosuccinimide (NBS) (5.50 g) and 2,2'-azobis(2-methylpropionitrile) (AIBN) (0.40 g) in carbon tetrachloride (50 ml) is heated under reflux for 2 hours, then cooled, filtered and concentrated in vacuo to give ethyl 4-chloro-2-(1-bromoethyl)-nicotinate.

A mixture of ethyl 4-chloro-2-(1-bromoethyl)nicotinate (7.45 g) and sodium bicarbonate (4.00 g) in 50 ml of DMSO is heated at 120°, under nitrogen, for 2 hours, after which it is cooled, diluted with water, filtered and extracted with ether. The combined organic layers are washed with water and concentrated. The residue is taken into ethyl acetate, washed with brine, dried, concentrated and purified by flash chromatography to give 4-chloro-7-methylfuro-[3,4-b]-pyridin-5-(7H)-one, which is then reacted with N-bromosuccinimide and 2,2'-azobis(2-methylpropionitrile), as above, to give 7-bromo-4-chloro-7-methylfuro-[3,4-b]-pyridin-5-(7H)-one.

A solution of lithium hydroxide monohydrate (0.27 g) in 20 ml of water is added to a slurry of the above lactone (1.20 g) in 40 ml of ethanol. The mixture is stirred at RT for 2.5 hours, and is then concentrated in vacuo. The residue is partitioned in 2N sulfuric acid and ethyl acetate, extracted with ethyl acetate, washed with brine, dried and purified to give 2-acetyl-4-chloronicotinic acid.

EXAMPLE 29

A mixture of sodium acetate (14.76 g, 180.0 mmol) and acetic anhydride (150 ml) is heated, under $N_2$, to 120° for 10 min., and is then chilled to 10°. 2-Ethyl-2-propenal dimethylhydrazone (11.36 g, 90.0 mmol) is added, followed by addition of bromomaleic anhydride (16.41 g, 92.7 mmol) and the reaction mixture is stirred at 10° for ca. 1 hour. The mixture is then diluted with methylene chloride and filtered, and the solid is rinsed with methylene chloride until colorless. The filtrate is concentrated to remove the solvent and to give 1,4-dihydro-1-dimethylamino-5-ethyl-2,3-pyridine-dicarboxylic anhydride.

The above anhydride is dissolved in THF, and 100 ml of 2M HCl is added. The mixture is stirred and the THF is distilled off. The residue is recrystallized from THF to give 5-ethyl-2,3-pyridinedicarboxylic acid.

A mixture of the above carboxylic acid (3.0 g, 15.37 mmol) and acetic anhydride (15 ml) is heated until the acid is dissolved. The mixture is then concentrated under vacuum, and the residue is dissolved in ether, stirred, filtered, concentrated and dried to give 5-ethyl-2,3-pyridinedicarboxylic anhydride.

Following the procedure of Example 30, 5-ethyl-2,3-pyridinedicarboxylic anhydride is treated with lithium methylsulfonylmethyl(methyl)cuprate(I) to give 2-acetyl-5-ethylnicotinic acid.

EXAMPLE 30

A mixture of 2-methoxycarbonylnicotinic acid (4.0 g) and thionyl chloride (30 ml) is heated under reflux until homogeneous. The remaining thionyl chloride is distilled off in vacuo to give 2-methoxycarbonylnicotinoyl chloride.

Lithium methylsulfonylmethyl(methyl)cuprate(I) is chilled to −78°, and 2-methoxycarbonylnicotinoyl chloride (3.2 g, 16.0 mmol) is slowly added, keeping the temperature at −65° to −70°. The mixture is stirred at −78° for 1 hour, after which aq. ammonium chloride is added. The mixture is warmed to RT, poured into water and ethyl acetate and extracted with ethyl acetate. The combined organic phases are dried and reduced and the product is purified by prep. TLC to give methyl 3-acetyl-2-pyridinecarboxylate.

To methyl 3-acetyl-2-pyridinecarboxylate (1.86 g) in 20 ml of ethanol is added lithium hydroxide monohydrate (10 mmol) in 20 ml of hot water. After 1 hour, conc. hydrochloric acid (1 ml) is added, and the mixture is reduced under vacuum. The resulting solid is extracted with hot methylene chloride, and the residue is stirred with 15 ml of THF for 1 hour at 60°, then filtered and dried to give 3-acetyl-2-pyridinecarboxylic acid.

EXAMPLE 31

Following the procedure of Example 30, 4-methoxycarbonylnicotinic acid is reacted with thionyl chloride to give 4-methoxycarbonylnicotinoyl chloride. A slurry of the above chloride (22.7 mmol) in 100 ml of monoglyme (ethylene glycol dimethyl ether) is added to a chilled mixture of the sodium salt of diethyl malonate (2.2 eq.) in monoglyme. The mixture is allowed to warm to RT and is stirred at RT for 4 hours. Aq. sodium bicarbonate is added and the mixture is extracted with ether. It is then acidified to pH 2–3 and again extracted with ether. The combined organic phases of the acid layer are dried, filtered and concentrated to give methyl 3-(diethylmalonyl-carbonyl)-isonicotinate, which is then reacted with lithium hydroxide mono-hydrate and then hydrochloric acid to give 3-acetylisonicotinic acid.

EXAMPLE 32

A mixture of diethyl 3-oxofuro-(3,4-c)pyridin-1-(3H)-ylidene malonate (3.21 g, 11.0 mmol), 50% sodium hydroxide (4.0 g, 50.0 mmol) and 25 ml of water is heated to 120° for 4 hours. Hydrochloric acid is added until the mixture is acidic, after which it is heated for 5 min. and then cooled to RT and reduced. The residue is extracted with methylene chloride, with methylene chloride/ethanol (9:1) and with hot ethanol. The combined organic extracts are reduced and extracted with THF/methanol. The residue is reduced to give 4-acetylnicotinic acid.

EXAMPLE 33

A mixture of ethyl 5-acetyl-2-hydroxy-4-pyrimidinecarboxylate (2.91 g, 13.8 mmol), phosphoryl chloride (11 ml, 118.0 mmol) and diethylaniline (3 ml, 18.0 mmol) is heated to reflux under $N_2$ for 45 min, after which it is cooled to RT and worked up. The residue is distilled, then dissolved in a small amount of methylene chloride and set aside to crystallize. The solid is then filtered, rinsed with methylene chloride and dried to give ethyl 5-acetyl-2-chloro-4-pyrimidinecarboxylate.

Following the procedure of Example 30, ethyl 5-acetyl-2-chloro-4-pyrimidinecarboxylate is reacted with lithium hydroxide monohydrate to give the corresponding lithium salt and then with hydrochloric acid to give 5-acetyl-2-chloro-4-pyrimidinecarboxylic acid.

EXAMPLE 34

To a mixture of the lithium salt of 5-acetyl-2-chloro-4-pyrimidinecarboxylic acid (1.1 g, 4.90 mmol) and sodium bicarbonate (0.5 g, 5.95 mmol) in 20 ml of water is added 10% palladium on carbon (0.1 g), and the reaction mixture is kept under $H_2$ overnight. It is then acidified with 1M hydrochloric acid (6 ml) and concentrated. The resulting solid is filtered, rinsed with water and dried to give 5-acetyl-4-pyrimidinecarboxylic acid.

EXAMPLE 35

Silica (Silica 60; 10 g) is added to 40 ml of methylene chloride. Sulfuric acid (0.15 g) and water (0.85 g) are added and the suspension is stirred for 5 min. until the water is absorbed. Ethyl 4-(1,1-diethoxyethyl)-5-pyrimidinecarboxylate is added and the mixture is stirred at RT for ca. 7 hours. The reaction mixture is filtered and rinsed with methylene chloride and with ethanol. The combined organic phases are reduced to give ethyl 4-acetyl-5-pyrimidinecarboxylate.

Following the procedure of Example 30, 4-acetyl-5-pyrimidinecarboxylate is reacted with lithium hydroxide monohydrate and with hydrochloric acid to give 4-acetyl-5-pyrimidinecarboxylic acid.

EXAMPLE 36

Following the procedure of Example 30, 3-methoxycarbonyl-2-pyrazinecarboxylic acid is reacted with thionyl chloride to make the corresponding acid chloride, which is then reacted with lithium methylsulfonylmethyl(methyl)cuprate (I) to give methyl 3-acetyl-2-pyrazinecarboxylate. This carboxylate is reacted with lithium hydroxide monohydrate and with hydrochloric acid to give 3-acetyl-2-pyrazinecarboxylic acid.

EXAMPLE 37

At 0°, a solution of anhydrous ferric chloride (2.7 g, 17.0 mmol) in 50 ml of nitromethane is added portionwise with stirring over a period of 5 hours to a mixture of 3-bromofuran (25.0 g, 170.0 mmol) and acetic anhydride (20.4 g, 200.0 mmol) in 50 ml of nitromethane. After addition is completed, the resulting mixture is stirred at RT for 17 hours and is then evaporated in vacuo. The residue is taken up in 200 ml of diethyl ether, treated with 3.0 g of activated charcoal and filtered. The filtrate is washed with 5% sodium bicarbonate and dried and the solvent is removed by rotoevaporation to give, after purification, 2-acetyl-3-bromofuran.

A well-stirred mixture of 2-acetyl-3-bromofuran (13.7 g, 72.0 mmol), ethylene glycol (5.9 g, 94.0 mmol), p-toluenesulfonic acid (p-TSOH; 20 mg) and benzene (50 ml) is refluxed for 9 hours, after which additional ethylene glycol (1.8 g, 29.0 mmol) and p-TSOH (5 mg) is added and the refluxing is continued a further 16 hours. The reaction mixture is then washed with sat. sodium bicarbonate and with water and is dried. The solvent is removed by rotoevaporation to give 2-(3-bromo-2-furyl)-2-methyl-1,3-dioxolane. To a solution of 1.6M butyllithium in hexane (38 ml) and dry diethylether (40 ml), under $N_2$, is added dropwise with stirring a solution of the above dioxolane (11.18 g, 48.0 mmol) in 40 ml of ether, keeping the temperature below −68°. After addition is completed, the mixture is stirred for 30 min. at −70°, and then a slurry of $CO_2$ (50.0 g) in 100 ml of dry diethyl ether is added. The mixture is kept at −65° for 15 min. and is then allowed to warm to 10°. Water is added, followed by 10% sodium carbonate. The phases are separated and the organic phase is extracted. The combined aqueous phases are acidified with conc. HCl and extracted with ether. The organic phases are combined and dried and the solvent is removed by rotoevaporation. The resulting product is suspended in 5% HCl (85 ml) and stirred at RT for 2 hours, then extracted with ether and the combined ether phases are dried and evaporated to dryness. The crude product is purified to give 2-acetyl-3-furancarboxylic acid.

EXAMPLE 38

Ethyl 3-amino-2-pentenoate (20 g) in 45 ml DMF is chilled to −78°. Phosphorus oxychloride (25.7 g) is added, keeping the temperature between −10° and −30°. A solid forms and the mixture is then diluted with 12 ml methylene chloride. The resulting mixture is rapidly added to a chilled solution of 51 gm sodium sulfide nonahydrate in 150 ml water. Methylene chloride is added to the orange mixture, and the mixture is stirred 1 hr at R.T. 12.5% Agueous sodium hypochloride (98 ml) is added, and is backwashed with water and with aqueous sodium thiosulfate, dried, filtered and stripped. The residue is distilled to yield ethyl 3-ethyl-4-isothiazole-carboxylate.

EXAMPLE 39

Following generally the procedure of Example 28, ethyl 3-ethyl-4-isothiazolecarboxylate is reacted with NBS and benzoyl peroxide to give ethyl 3-(1-bromoethyl)-4-isothiazolecarboxylate, which is then reacted with sodium bicarbonate and DMSO and the resulting ethyl 3-acetyl-4-isothiazolecarboxy-late is treated with lithium hydroxide monohydrate to yield 3-acetyl-4-isothiazole-carboxylic acid.

EXAMPLE 40

Following the procedure of Example 28, methyl 4-ethyl-5-thiazolecarboxylate is reacted with NBS and AIBN to give methyl 4-(1-bromoethyl)-5-thiazolecarboxylate, which is then reacted with sodium bicarbonate, or alternatively with potassium carbonate, and DMSO and the resulting methyl 4-acetyl-5-thiazolecarboxylate is treated with lithium hydroxide monohydrate to yield 4-acetyl-5-thiazolecarboxylic acid.

EXAMPLE 41

To a solution of 138 mg of phenyl chloroformate in 1.4 mL of $CH_2Cl_2$ is added a solution of 103 mg of 3,5-difluoroanaline and 88 mg of triethylamine in 1.4 mL of $CH_2Cl_2$. The resulting mixture is stirred at room temperature for 2 h, then washed with saturated sodium bicarbonate and brine, and dried ($Na_2SO_4$). Removal of solvent in vacuo to give O-phenyl 3,5-difluorophenylcarbamate: m.p. 123°–125° C.

To a solid 100 mg of O-phenyl 3,5-difluorophenylcarbamate 0.7 mL of hydrazine monohydrate was added. After stirring for 3 h at room temperature a white solid is collected by filtration, washed with water and ether. Removal of traces of the solvents in vacuo gives 4-(3,5-difluorophenyl)-semicarbazide: m.p. 177°–179° C.

EXAMPLE 42

Potassium fluoride (240 gms Aldrich spray dried) and tetramethylene sulfone (500 gms) are placed in a two liter flask. The mixture is dehydrated by adding and distilling toluene from the flask. Then 3,5-dichlorobenzonitrile (132 gms) and 1,3-dinitrobenzene (3 gms) are added and the mixture heated under nitrogen for 29.5 hrs at 225°. After cooling to room temperature the mixture is diluted with water (1000 ml), shaken with toluene (350 ml) and filtered through a celite pad to remove insoluble solids. The layers are separated and the aqueous layer extracted with a second portion of toluene. The combined toluene layers are backwashed with water (2X1L). Toluene is distilled out at 40 mm pressure and the solid remaining partly sublimed (Kugelrohr, 65° at 8 mm pressure) to remove 3,5-difluorobenzonitrile. The reaction was repeated and the two batches of pot material are distilled through a 430×20 mm column filled with glass helices at 70°–80° and 8 mm to give 3-chloro-5-fluorobenzonitrile as a volatile white solid.

EXAMPLE 43

A mixture of sulfuric acid (500 ml) and water (100 ml) is heated to 95° and 3-chloro-5-fluorobenzonitrile (94.8 gms) added. After 4 hours the mixture is cooled and poured over ice and water added to make 3.6 L. In 1.2 L portions the mixture is filtered, the solid rinsed with hexane and the aqueous rinsed with hexane (4×120 ml) then extracted with ethyl acetate (2×100 ml). The solid and the ethyl acetate extracts were combined, dried over magnesium sulfate and stripped to give 3-chloro-5-fluorobenzamide as a white solid.

EXAMPLE 44

A 25% solution of sodium methoxide in methanol (375 gsm, 1.74M) and methanol (800 ml) are placed in a 3 L flask and chilled to −55°. Bromine (94 gms, 0.588M) is added slowly while the temperature is held between −53° and −55°. The reaction mixture is a clear yellow solution. 3-Chloro-5-fluorobenzamide (100.3 gms, 0.578M) in methanol (500 ml) is added while the temperature is held between −55° and −50° to give a colorless reaction mixture. The mixture is allowed to warm slowly to room temperature and then heated to reflux for five hours. After cooling to room temperature and neutralizing with acetic acid the mixture is stripped to a solid. The solid is dissolved in water and extracted with ethyl ether (2×). The ether is backwashed with water and stripped to a solid which is recrystallized twice from methanol/water to give N-methoxycarbonyl-3-chloro-5-fluoroaniline as a white solid.

EXAMPLE 45

N-methoxycarbonyl-3-chloro-5-fluoroaniline (51.8 gms, 254M) is added to a mixture of hydrazine hydrate (125 ml) and isobutyl alcohol (160 ml). The mixture is heated to 100° for 10 hours under nitrogen. The solution is cooled to room temperature, diluted with water and filtered. The solid is rinsed with water (2×) and dried under vacuum to give 4-(3-chloro-5-fluorophenyl)-semicarbazide as a white solid.

COMPOSITION EXAMPLES

EXAMPLE 46

A. Water dispersible powder

The sodium salt or the isopropylammonium salt of compound 4 is dissolved to the desired percentage concentration in water containing 0.5% surfactant (e.g., a 1:1:1 mixture of sorbitan monolaurate:polyoxyethylene[20]sorbitan monolaurate:polyoxyethylene[20-]sorbitan trioleate).

B. Suspension concentrate—26%

| | |
|---|---|
| sodium salt of cpd. 30 | 26% |
| propylene glycol | 73% |
| octyl phenoxypoly[ethyleneoxy]ethanol | 1% |

The above components are mixed and wet-milled to 5–10 micron particle size.

C. Wettable powder—50%

| | |
|---|---|
| sodium salt of cpd. 30 | 50% |
| sodium lignosulfonate | 4% |
| sodium dialkylnaphthalene sulfonate | 1% |
| kaolin | 45% |

The above components are mixed and wet-milled. The resulting mixture is added to water for spraying.

BIOLOGICAL ACTIVITY

EXAMPLE 47

Pre-emergent herbicidal activity of selected compounds of the present invention was determined as follows: Seeds of selected weeds were planted and the soil was drenched with a solution of water (17%), surfactant (0.17%) and the test compound at a rate equivalent to 10 lb/acre. Scoring was made two weeks after treatment. The grasses (GR) green foxtail, watergrass, shattercane and wild oats and the broadleafs (BL) annual morning glory, mustard, nightshade and velvetleaf were treated. The average pre-emergent activity of the compounds is presented in Table G below.

EXAMPLE 48

Post-emergence herbicidal activity of selected compounds of the present invention was tested as follows: Seedlings of selected weeds were sprayed with a solution of water/acetone (1:1), surfactant (0.5%) and the test compound at a rate equivalent to 10 lb/acre. Scoring was made two weeks after spraying. The grasses (GR) green foxtail, watergrass, shattercane and wild oats and the broadleafs (BL) annual morning glory, mustard, soybean and velvetleaf were treated. The average post-emergent activity of the compounds are presented in Table I below.

TABLE I

| | % Herbicidal Activity at 10 lb/Acre | | | |
|---|---|---|---|---|
| | Pre | | Post | |
| Compound No. | GR | BL | GR | BL |
| 1 | 91 | 86 | 48 | 61 |
| Na salt of 1 | 88 | 93 | 47 | 62 |
| 3 | 96 | 90 | 58 | 75 |
| Na salt of 3 | 93 | 89 | 63 | 81 |
| 4 | 91 | 91 | 72 | 85 |
| Na salt of 4 | 94 | 89 | 81 | 85 |
| NH$_4$ salt of 4 | 92 | 92 | 77 | 78 |
| isoprop NH$_3$ salt of 4 | 77 | 80 | 61 | 77 |
| diisoprop NH$_3$ salt of 4 | 82 | 80 | 63 | 80 |
| 22 | 58 | 58 | 30 | 71 |
| Na salt of 22 | 53 | 73 | 20 | 56 |
| 23 | 75 | 63 | 53 | 70 |
| Na salt of 23 | 68 | 80 | 66 | 73 |
| 24 | 92 | 86 | 55 | 76 |
| Na salt of 24 | 85 | 82 | 63 | 75 |
| 25 | 90 | 68 | 68 | 81 |
| Na salt of 25 | 79 | 90 | 66 | 85 |
| 30 | 96 | 87 | 78 | 86 |
| Na salt of 30 | 100 | 89 | 83 | 90 |
| 31 | 87 | 83 | 80 | 87 |
| Na salt of 31 | 96 | 100 | 71 | 86 |
| 2-(2-hydroxyethoxy)ethyl- ammonium colt of 31 | 91 | 88 | 71 | 79 |
| 32 | 92 | 95 | 90 | 95 |
| Na salt of 32 | 96 | 94 | 86 | 90 |
| 55 | 80 | 80 | 76 | 82 |
| 57 | 85 | 90 | 63 | 85 |
| 60 | 85 | 80 | 71 | 78 |
| 61 | 82 | 81 | 67 | 81 |
| 110 | 88 | 76 | — | — |
| Na salt of 110 | 81 | 80 | 60 | 80 |

What is claimed is:

1. A compound of the formula (A):

$$R-C=N-N-R^2 \quad (A)$$
$$\phantom{R-C=N-}|\phantom{N-}|$$
$$\phantom{R-C=N-}R^3\phantom{N-}R^4$$

wherein,

R is the group

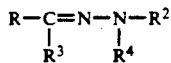

R$^1$ is the group

R$^2$ is the group

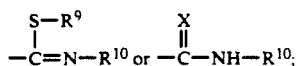

each of R$^3$ and R$^4$ is independently hydrogen or lower alkyl;

R$^5$ is hydrogen; C$_{1-8}$alkyl; C$_{1-8}$haloalkyl; C$_{2-10}$alkoxyalkyl; unsubstituted phenyl;-phenyl substituted at one to three of the ring carbon atoms with a group selected from C$_{1-8}$alkyl, C$_{1-8}$haloalkyl, C$_{1-8}$alkoxy, C$_{1-8}$haloalkoxy or halogen; alkali or alkali earth cation; ammonium cation, unsubstituted or substituted by a C$_{1-20}$alkyl, di-C$_{1-20}$alkyl, tri-C$_{1-20}$alkyl, tetra-C$_{1-20}$alkyl, hydroxy-C$_{1-5}$alkyl, di(hydroxy-C$_{1-5}$alkyl), tri(hydroxy-C$_{1-5}$alkyl), C$_{1-5}$alkoxy-C$_{1-5}$alkyl, hydroxy-C$_{1-5}$alkoxy-C$_{1-5}$alkyl or C$_{1-5}$alkoxycarbonyl-C$_{1-5}$alkyl group; phosphonium cation; tri-C$_{1-5}$alkylsulfonium cation; tri-C$_{1-8}$alkylsulfoxonium cation or the group

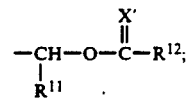

each of R$^6$ and R$^9$ is lower alkyl, lower alkenyl, phenyl or benzyl;

each of R$^7$ and R$^8$ is independently hydrogen or lower alkyl; or R$^7$ and R$^8$ are taken together to form a lower alkylene bridge of three to six carbon atoms, optionally including one of O, S or NH in the ring;

R$^{10}$ is the group

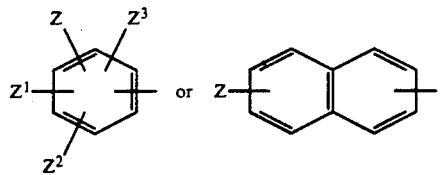

each of R$^{11}$ and R$^{12}$ is independently hydrogen or C$_{1-8}$alkyl or lower alkoxyalkyl;

m is zero or one;

each of X and X' is independently oxygen or sulfur; and each of Y, Z, Z$^1$, Z$^2$ and Z$^3$ is independently hydrogen, C$_{1-8}$alkyl, C$_{1-8}$haloalkyl, C$_{1-8}$alkoxy, C$_{1-8}$haloalkoxy, C$_{2-8}$alkenyloxy, C$_{2-8}$haloalkenyloxy, C$_{2-8}$alkynyloxy, C$_{2-8}$alkylthio, phenyl, phenoxy, hydroxy, halogen, nitro, cyano, amino, lower alkylamino or dialkylamino.

2. A compound of the following formula, according to claim 1

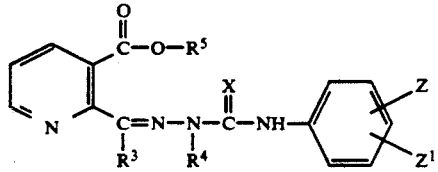

3. A compound according to claim 2 wherein R$^3$ is methyl or ethyl; R$^4$ is hydrogen, methyl or ethyl.

4. A compound according to claim 1 wherein each of $R^7$ and $R^8$ is independently hydrogen or $C_{1-8}$alkyl; or $R^7$ and $R^8$ are taken together to form a lower alkylene bridge of three to six carbon atoms.

5. A compound according to claim 4 wherein $R^3$ is methyl or ethyl; and $R^4$ is hydrogen, methyl or ethyl.

6. A compound according to claim 3 wherein Z and $Z^1$ are independently hydrogen, $C_{1-8}$alkyl, $C_{1-8}$haloalkyl, $C_{1-8}$alkoxy, $C_{1-8}$haloalkoxy, $C_{2-8}$alkenyloxy, $C_{2-8}$haloalkenyloxy, $C_{2-8}$alkynyloxy, phenyl, phenoxy, $C_{1-8}$alkylthio, hydroxy, halogen, nitro or cyano; $R^5$ is hydrogen, $C_{1-8}$alkyl, $C_{1-8}$haloalkyl, $C_{2-10}$alkoxyalkyl, alkali earth cation, ammonium cation, substituted ammonium cation, phosphonium cation, tri-$C_{1-8}$alkylsulfonium cation, tri-$C_{1-8}$alkylsulfoxonium cation, or the group —CH($R^{11}$)—O—C(=X')-$R^{12}$; each of $R^{11}$ and $R^{12}$ is independently hydrogen or $C_{1-8}$alkyl; and X' is oxygen or sulfur.

7. A compound according to claim 3 wherein Z is hydrogen, methyl, methoxy, ethyl, bromo, chloro, fluoro, iodo, trifluoromethyl or trifluoromethoxy; and $Z^1$ hydrogen, chloro, fluoro, methyl or methoxy.

8. A compound according to claim 7 wherein X is oxygen.

9. A compound according to claim 8 wherein $R^5$ is hydrogen, an alkali metal cation, an ammonium cation or a substituted ammonium cation.

10. A compound according to claim 8 wherein $R^5$ is hydrogen, sodium cation, ammonium cation, $C_{1-20}$alkylammonium cation, di-$C_{1-5}$alkylammonium cation, hydroxy-$C_{1-5}$alkylammonium cation, di-(hydroxy-$C_{1-5}$alkyl)ammonium cation, hydroxy-$C_{1-5}$alkoxy-$C_{1-5}$alkylammonium cation or the group

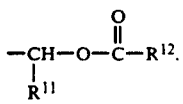

11. A compound according to claim 10 wherein $R^3$ is methyl; $R^4$ is hydrogen; $R^{11}$ is hydrogen, methyl, ethyl or sec-butyl; and $R^{12}$ is hydrogen, methyl, ethyl, n-propyl, sec-butyl or tert-butyl.

12. A compound according to claim 11 wherein $R^5$ is hydrogen, sodium cation, isopropylammonium cation, tetradecylammonium cation, 2-hydroxyethylammonium cation, di-2-hydroxyethylammonium cation, 2-(2-hydroxyethoxy)ethylammonium cation, butyryloxymethyl, 1-(2-methylbutyryloxy)ethyl, pivaloyloxymethyl, 1-(pivaloyloxy)ethyl or 1-(propionyloxy)ethyl.

13. A compound according to claim 12 wherein Z is hydrogen and $Z^1$ is hydrogen.

14. A compound according to claim 12 wherein Z is 3-chloro or 3-fluoro and $Z^1$ is hydrogen.

15. A compound according to claim 14 wherein Z is 3-fluoro.

16. A compound according to claim 14 wherein $R^5$ is hydrogen, sodium cation, isopropylammonium cation, 2-(2-hydroxyethoxy)ethylammonium cation, 2-hydroxyethylammonium cation or di-2-hydroxyethylammonium cation.

17. A compound according to claim 14 wherein Z is 3-chloro.

18. A compound according to claim 17 wherein $R^5$ is hydrogen, tetradecylammonium cation or di-2-hydroxyethylammonium cation.

19. A compound according to claim 17 wherein $R^5$ is sodium cation.

20. A compound according to claim 12 wherein Z is 3-chloro or 3-fluoro and $Z^1$ is 5-chloro or 5-fluoro.

21. A compound according to claim 20 wherein Z is 3-chloro and $Z^1$ is 5-chloro.

22. A compound according to claim 20 wherein Z is 3-fluoro and $Z^1$ is 5-fluoro.

23. A compound according to claim 22 wherein $R^5$ is hydrogen, sodium cation, isopropylammonium cation or 2-(2-hydroxyethoxy)ethylammonium cation.

24. A compound according to claim 9 wherein $R^3$ is methyl, $R^4$ is hydrogen, Z is hydrogen, 3-chloro or 3-fluoro and $Z^1$ is hydrogen, 5-chloro or 5-fluoro.

25. The compound 2-acetylnicotinic acid 4-(3-fluorophenyl)semicarbazone, according to claim 16.

26. The compound, the sodium salt of 2-acetylnicotinic acid 4-(3-fluorophenyl)semicarbazone, according to claim 16.

27. The compound, the isopropylammonium salt of 2-acetylnicotinic acid 4-(3-fluorophenyl)semicarbazone, according to claim 16.

28. The compound, the 2-(2-hydroxyethoxy)ethylammonium salt of 2-acetylnicotinic acid 4-(3-fluorophenyl)semicarbazone, according to claim 16.

29. The compound, the di-2-hydroxyethylammonium salt of 2-acetylnicotinic acid 4-(3-fluorophenyl)semicarbazone, according to claim 16.

30. The compound, the tetradecylammonium salt of 2-acetylnicotinic acid 4-(3-chlorophenyl)semicarbazone, according to claim 18.

31. The compound 2-acetylnicotinic acid 4-(3,5-difluorophenyl)-semicarbazone, according to claim 23.

32. The compound, the sodium salt of 2-acetylnicotinic acid 4-(3,5-difluorophenyl)semicarbazone, according to claim 23.

33. The compound, the 2-(2-hydroxyethoxy)ethylammonium salt of 2-acetylnicotinic acid 4-(3,5-difluorophenyl)semicarbazone, according to claim 23.

34. A herbicidal composition comprising a herbicidally effective amount of a compound according to claim 1 together with suitable liquid and solid carrier.

35. A method for combatting weeds which comprises treating said weed or its locus with a herbicidally effective amount of a compound according to claim 1.

* * * * *